(12) United States Patent
Himmelsbach et al.

(10) Patent No.: US 7,879,806 B2
(45) Date of Patent: Feb. 1, 2011

(54) GLUCOPYRANOSYL-SUBSTITUTED BENZYL-BENZONITRILE DERIVATES, MEDICAMENTS CONTAINING SUCH COMPOUNDS, THEIR USE AND PROCESS FOR THEIR MANUFACTURE

(75) Inventors: Frank Himmelsbach, Mittelbiberach (DE); Matthias Eckhardt, Biberach (DE); Peter Eickelmann, Mittelbiberach (DE); Leo Thomas, Biberach (DE)

(73) Assignee: Boehringer Ingelheim International GmbH, Ingelheim am Rheim (DE)

( * ) Notice: Subject to any disclaimer, the term of this patent is extended or adjusted under 35 U.S.C. 154(b) by 0 days.

(21) Appl. No.: 12/513,592

(22) PCT Filed: Nov. 5, 2007

(86) PCT No.: PCT/EP2007/061877

§ 371 (c)(1),
(2), (4) Date: Jul. 9, 2009

(87) PCT Pub. No.: WO2008/055870

PCT Pub. Date: May 15, 2008

(65) Prior Publication Data

US 2010/0069310 A1 Mar. 18, 2010

(30) Foreign Application Priority Data

Nov. 6, 2006 (EP) .................................. 06123515
Feb. 21, 2007 (EP) .................................. 07102828
Jun. 6, 2007 (EP) .................................. 07109727

(51) Int. Cl.
*A01N 43/04* (2006.01)
*A61K 31/70* (2006.01)
*C07H 1/00* (2006.01)

(52) U.S. Cl. .................. 514/23; 536/1.11; 536/18.7
(58) Field of Classification Search .................. None
See application file for complete search history.

(56) References Cited

U.S. PATENT DOCUMENTS

| | | |
|---|---|---|
| 7,393,836 B2 | 7/2008 | Eckhardt et al. |
| 7,417,032 B2 | 8/2008 | Eckhardt et al. |
| 7,419,959 B2 | 9/2008 | Eckhardt et al. |
| 7,579,449 B2 | 8/2009 | Eckhardt et al. |
| 7,683,160 B2 | 3/2010 | Eckhardt et al. |
| 7,687,469 B2 | 3/2010 | Eckhardt et al. |
| 7,713,938 B2 | 5/2010 | Himmelsbach et al. |
| 7,723,309 B2 | 5/2010 | Himmelsbach et al. |
| 2005/0209166 A1* | 9/2005 | Eckhardt et al. ............. 514/23 |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0074031 A1 | 4/2006 | Eckhardt et al. |
| 2006/0142210 A1 | 6/2006 | Eckhardt et al. |
| 2006/0189548 A1 | 8/2006 | Himmelsbach et al. |
| 2006/0234953 A1 | 10/2006 | Himmelsbach et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0049537 A1 | 3/2007 | Eckhardt et al. |
| 2007/0054867 A1 | 3/2007 | Eckhardt et al. |
| 2007/0073046 A1 | 3/2007 | Eckhardt et al. |
| 2007/0249544 A1 | 10/2007 | Himmelsbach et al. |
| 2007/0259821 A1 | 11/2007 | Eckhardt et al. |
| 2008/0058379 A1 | 3/2008 | Eckhardt et al. |
| 2009/0023913 A1 | 1/2009 | Eckhardt et al. |
| 2009/0318547 A1 | 12/2009 | Eckhardt et al. |
| 2009/0326215 A1 | 12/2009 | Eckhardt et al. |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |

FOREIGN PATENT DOCUMENTS

| | | |
|---|---|---|
| CA | 2 557 801 A1 | 10/2005 |
| WO | 2005/092877 A1 | 10/2005 |

OTHER PUBLICATIONS

Adachi et al., Metabolism, vol. 49, No. 8, Aug. 2000, pp. 990-995.*
International Search Report for PCT/EP2007/061877 mailed Feb. 5, 2008.
U.S. Appl. No. 12/377,217, filed Mar. 30, 2009.
U.S. Appl. No. 12/513,763, filed May 6, 2009.
U.S. Appl. No. 12/446,003, filed Jul. 9, 2009.
U.S. Appl. No. 12/673,319, filed Feb. 12, 2010.
U.S. Appl. No. 12/673,327, filed Feb. 12, 2010.
U.S. Appl. No. 12/704,042, filed Feb. 11, 2010.
U.S. Appl. No. 12/704,062, filed Feb. 11, 2010.
U.S. Appl. No. 12/796,866, filed Jun. 9, 2010.

* cited by examiner

*Primary Examiner*—Traviss C McIntosh, III
(74) *Attorney, Agent, or Firm*—Michael P. Morris; Edward S. Lazer; Edouard G. Lebel

(57) ABSTRACT

Glucopyranosyl-substituted benzyl-benzonitrile derivatives of general formula (I) as defined according to claim 1, including the tautomers, the stereoisomers thereof, the mixtures thereof and the salts thereof. The compounds according to the invention are suitable for the treatment of metabolic disorders.

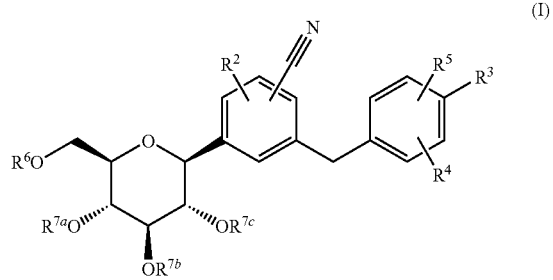

(I)

16 Claims, No Drawings

GLUCOPYRANOSYL-SUBSTITUTED BENZYL-BENZONITRILE DERIVATES, MEDICAMENTS CONTAINING SUCH COMPOUNDS, THEIR USE AND PROCESS FOR THEIR MANUFACTURE

This application is the national phase entry under 35 U.S.C. §371 of International Application No. PCT/EP2007/061877, filed Nov. 5, 2007, which claims priority to European Applications No. EP 06123515.6, filed Nov. 6, 2006; EP 07102828.6. filed Feb. 21, 2007 and EP 07109727.3, filed Jun. 6, 2007, each of which is hereby incorporated by reference in its entirety.

The present invention relates to glucopyranosyl-substituted benzyl-benzonitrile derivatives of the general formula I

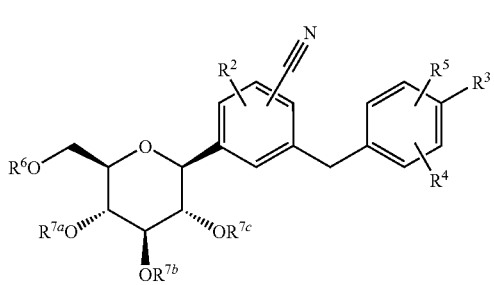

wherein the groups $R^2$ to $R^6$ and $R^{7a}$, $R^{7b}$, $R^{7c}$ are as defined hereinafter, including the tautomers, the stereoisomers, the mixtures thereof and the salts thereof. The invention further relates to pharmaceutical compositions containing a compound of formula I according to the invention as well as the use of a compound according to the invention for preparing a pharmaceutical composition for the treatment of metabolic disorders. In addition, the invention relates to processes for preparing a pharmaceutical composition as well as a compound according to the invention.

In the literature, compounds which have an inhibitory effect on the sodium-dependent glucose cotransporter SGLT2 are proposed for the treatment of diseases, particularly diabetes.

Glucopyranosyloxy- and glucopyranosyl-substituted aromatic groups and the preparation thereof and their possible activity as SGLT2 inhibitors are known from published International applications WO 98/31697, WO 01/27128, WO 02/083066, WO 03/099836, WO 2004/063209, WO 2004/080990, WO 2004/013118, WO 2004/052902, WO 2004/052903, WO 2005/092877, WO 06/010557, WO 06/018150, WO 06/037537, WO 06/089872, WO 2006/064033, WO 2007/093610 and US application US 2003/0114390.

AIM OF THE INVENTION

The aim of the present invention is to find new pyranosyl-substituted benzonitrile derivatives, particularly those which are active with regard to the sodium-dependent glucose cotransporter SGLT, particularly SGLT2. A further aim of the present invention is to discover pyranosyl-substituted benzene derivatives which have a good to very good inhibitory effect on the sodium-dependent glucose cotransporter SGLT2 in vitro and/or in vivo and/or have good to very good pharmacological and/or pharmacokinetic and/or physicochemical properties.

A further aim of the present invention is to provide new pharmaceutical compositions which are suitable for the prevention and/or treatment of metabolic disorders, particularly diabetes.

The invention also sets out to provide a process for preparing the compounds according to the invention.

Other aims of the present invention will become apparent to the skilled man directly from the foregoing and following remarks.

OBJECT OF THE INVENTION

In a first aspect the present invention relates to glucopyranosyl-substituted benzyl-benzonitrile derivatives of general formula I

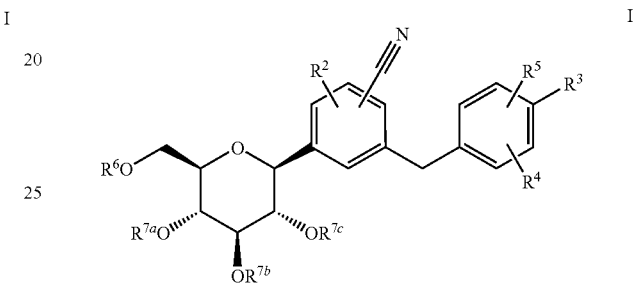

wherein $R^2$ denotes fluorine, chlorine, bromine, iodine, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, hydroxy, $C_{1-4}$-alkoxy, $C_{3-7}$-cycloalkyloxy, $C_{5-7}$-cycloalkenyloxy, $C_{1-4}$-alkylsulfanyl, amino, nitro or cyano, while the above-mentioned alkyl-, alkenyl-, alkynyl-, cycloalkyl-und cycloalkenyl-residues may be mono- or polysubstituted by fluorine and/or mono- or disubstituted by identical or different substituents L2, and while in the above-mentioned $C_{5-6}$-cycloalkyl and $C_{5-6}$-cycloalkenyl rings one or two methylene groups may be replaced independently of one another by O, S, CO, SO or $SO_2$, and $R^3$ hydrogen, fluorine, chlorine, bromine, iodine, $C_{1-6}$-alkyl, $C_{2-6}$-alkynyl, $C_{2-6}$-alkenyl, $C_{3-7}$-cycloalkyl, $C_{3-7}$-cycloalkyl-$C_{1-3}$-alkyl, $C_{5-7}$-cycloalkenyl, $C_{5-7}$-cycloalkenyl-$C_{1-3}$-alkyl, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, hydroxycarbonyl, $C_{1-4}$-alkoxycarbonyl, $C_{1-4}$-alkyl-amino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, arylcarbonylamino, hetero-arylcarbonylamino, $C_{1-4}$-alkylsulfonylamino, arylsulfonylamino, $C_{1-6}$-alkoxy, $C_{3-7}$-cycloalkyloxy, $C_{5-7}$-cycloalkenyloxy, aryloxy, heteroaryloxy, $C_{1-4}$-alkylsulfanyl, $C_{1-4}$-alkylsulfinyl, $C_{1-4}$-alkylsulfonyl, $C_{3-7}$-cycloalkylsulfanyl, $C_{3-7}$-cycloalkylsulfinyl, $C_{3-7}$-cycloalkylsulfonyl, $C_{5-7}$-cycloalkenylsulfanyl, $C_{5-7}$-cycloalkenylsulfinyl, $C_{5-7}$-cycloalkenylsulfonyl, arylsulfanyl, arylsulfinyl, arylsulfonyl, heteroarylsulfanyl, heteroarylsulfinyl, heteroarylsulfonyl, amino, hydroxy, cyano and nitro, while the above-mentioned alkyl-, alkenyl-, alkynyl-, cycloalkyl- and cycloalkenyl-residues may be mono- or polysubstituted by fluorine and/or mono- or disubstituted by identical or different substituents L2, and while in the above-mentioned $C_{5-6}$-cycloalkyl and $C_{5-6}$-cycloalkenyl rings one or two methylene groups may be replaced independently of one another by O, S, CO, SO or $SO_2$, and while in the above-mentioned N-heterocycloalkyl rings one methylene group may be replaced by CO or $SO_2$, and $R^4$, $R^5$ independently of one another denote hydrogen, fluorine, chlorine, bromine, iodine, cyano, nitro, $C_{1-3}$-alkyl, $C_{1-3}$-alkoxy, or a methyl- or methoxy-group substituted by 1 to 3 fluorine atoms, L1 independently of one another are selected from among fluorine, chlorine, bromine, iodine, hydroxy, cyano, $C_{1-3}$-alkyl, difluoromethyl, trifluoromethyl, $C_{1-3}$-alkoxy, difluoromethoxy, trifluoromethoxy, amino, $C_{1-3}$-alkyl-amino and di($C_{1-3}$-alkyl)amino; and L2 independently of one another are selected from among fluorine, chlorine, hydroxy, hydroxyl-$C_{1-4}$-alkyl, $C_{1-4}$-alkoxy, trifluoromethoxy, $C_{1-4}$-alkoxy-$C_{1-4}$-alkyl, cyano, hydroxycarbonyl, ($C_{1-4}$-alkyl)oxycarbonyl, aminocarbonyl, $C_{1-4}$-alkyl, trifluoromethyl, amino, $C_{1-4}$-alkyl-carbonylamino, $C_{1-3}$-alkyl-amino and di($C_{1-3}$-alkyl)-amino; and $R^6$, $R^{7a}$, $R^{7b}$, $R^{7c}$ independently of one another have a meaning selected from among hydrogen, ($C_{1-18}$-alkyl)carbonyl, ($C_{1-18}$-alkyl)oxycarbonyl, arylcarbonyl and aryl-($C_{1-3}$-alkyl)-carbonyl, while the aryl-groups may be mono- or disubstituted independently of one another by identical or different groups L1;

while by the aryl groups mentioned in the definition of the above groups are meant phenyl or naphthyl groups which may be substituted as defined; and while, unless otherwise stated, the above-mentioned alkyl groups may be straight-chain or branched, the tautomers, the stereoisomers thereof, the mixtures thereof and the salts thereof.

The compounds of general formula I according to the invention and the physiologically acceptable salts thereof have valuable pharmacological properties, particularly an inhibitory effect on the sodium-dependent glucose cotransporter SGLT, particularly SGLT2. Moreover compounds according to the invention may have an inhibitory effect on the sodium-dependent glucose cotransporter SGLT1. Compared with a possible inhibitory effect on SGLT1 the compounds according to the invention preferably inhibit SGLT2 selectively.

The present invention also relates to the physiologically acceptable salts of the compounds according to the invention with inorganic or organic acids.

This invention also relates to pharmaceutical compositions, containing at least one compound according to the invention or a physiologically acceptable salt according to the invention, optionally together with one or more inert carriers and/or diluents.

This invention also relates to the use of at least one compound according to the invention or one of the physiologically acceptable salts thereof for preparing a pharmaceutical composition which is suitable for the treatment or prevention of diseases or conditions which can be influenced by inhibiting the sodium-dependent glucose cotransporter SGLT, particularly SGLT2.

This invention also relates to the use of at least one compound according to the invention or one of the physiologically acceptable salts thereof for preparing a pharmaceutical composition which is suitable for the treatment of metabolic disorders.

In a further aspect the present invention relates to the use of at least one compound according to the invention or one of the physiologically acceptable salts thereof for preparing a pharmaceutical composition for preventing the degeneration of pancreatic beta cells and/or for improving and/or restoring the functionality of pancreatic beta cells.

In a further aspect the present invention relates to a use of at least one compound according to the invention or one of the physiologically acceptable salts thereof for preparing a pharmaceutical composition for preventing, slowing, delaying or treating diseases or conditions attributed to an abnormal accumulation of liver fat in a patient in need thereof.

This invention also relates to the use of at least one compound according to the invention or one of the physiologically acceptable salts thereof for preparing a pharmaceutical composition for inhibiting the sodium-dependent glucose cotransporter SGLT, particularly SGLT2.

The invention further relates to a process for preparing a pharmaceutical composition according to the invention, characterised in that a compound according to the invention or one of the physiologically acceptable salts thereof is incorporated in one or more inert carriers and/or diluents by a non-chemical method.

The present invention also relates to a process for preparing the compounds of general formula I according to the invention, characterised in that a) in order to prepare compounds of general formula I which are defined as hereinbefore and hereinafter, a compound of general formula II

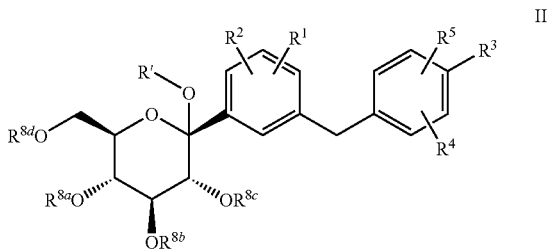

wherein $R^1$ denotes cyano, chlorine or bromine;

R' denotes H, $C_{1-4}$-alkyl, ($C_{1-18}$-alkyl)carbonyl, ($C_{1-18}$-alkyl)oxycarbonyl, arylcarbonyl and aryl-($C_{1-3}$-alkyl)-carbonyl, wherein the alkyl or aryl groups may be mono- or polysubstituted by halogen;

$R^{8a}$, $R^{8b}$, $R^{8c}$, $R^{8d}$ independently of one another have one of the meanings given hereinbefore and hereinafter for the groups $R^6$, $R^{7a}$, $R^{7b}$, $R^{7c}$, or denote a benzyl or allyl group or a $R^aR^bR^cSi$ group or a ketal or acetal group, particularly an alkylidene or arylalkylidene ketal or acetal group, while in each case two adjacent groups $R^{8a}$, $R^{8b}$, $R^{8c}$, $R^{8d}$ may form a cyclic silyl ketal, ketal or acetal group or a 1,2-di($C_{1-3}$-alkoxy)-1,2-di($C_{1-3}$-alkyl)-ethylene bridge, while the above-mentioned ethylene bridge forms, together with two oxygen atoms and the two associated carbon atoms of the pyranose ring, a substituted dioxane ring, particularly a 2,3-dimethyl-2,3-di($C_{1-3}$-alkoxy)-1,4-dioxane ring, and while alkyl, aryl and/or benzyl groups may be mono- or polysubstituted by halogen or $C_{1-3}$-alkoxy, and while benzyl groups may also be substituted by a di-($C_{1-3}$-alkyl) amino group; and $R^a$, $R^b$, $R^c$ independently of one another denote $C_{1-4}$-alkyl, aryl or aryl-$C_{1-3}$-alkyl, wherein the aryl or alkyl groups may be mono- or polysubstituted by halogen;

while by the aryl groups mentioned in the definition of the above groups are meant phenyl or naphthyl groups, preferably phenyl groups;

and wherein the groups $R^2$ to $R^6$, $R^{7a}$, $R^{7b}$, $R^{7c}$ are defined as hereinbefore and hereinafter;

is reacted with a reducing agent in the presence of a Lewis or Brønsted acid, while any protective groups present are cleaved simultaneously or subsequently; if in the compound of the formula II $R^1$ denotes Cl or Br, then in a subsequent transformation the respective halogen atom of $R^1$ is replaced by a cyano group; or b) in order to prepare compounds of general formula I wherein $R^6$, $R^{7a}$, $R^{7b}$ and $R^{7c}$ denote hydrogen, a compound of general formula III

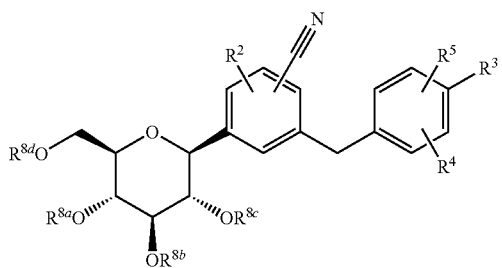

wherein $R^{8a}$, $R^{8b}$, $R^{8c}$, $R^{8d}$ and $R^2$ to $R^5$ are defined as hereinbefore and hereinafter, but at least one of the groups $R^{8a}$, $R^{8b}$, $R^{8c}$, $R^{8d}$ does not denote hydrogen, is hydrolysed, and if desired a compound of general formula I thus obtained wherein $R^6$ denotes a hydrogen atom, is converted by acylation into a corresponding acyl compound of general formula I, and/or if necessary any protective group used in the reactions described above is cleaved and/or if desired a compound of general formula I thus obtained is resolved into its stereoisomers and/or if desired a compound of general formula I thus obtained is converted into the salts thereof, particularly for pharmaceutical use into the physiologically acceptable salts thereof.

This invention further relates to a process for preparing compounds of general formula II

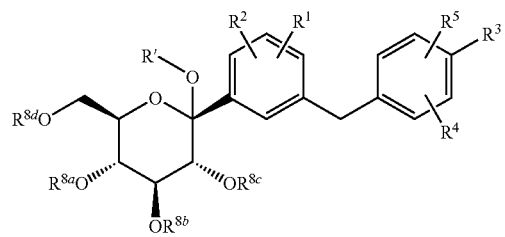

wherein
$R^1$ denotes cyano, chlorine or bromine;
R' denotes H, $C_{1-4}$-alkyl, ($C_{1-18}$-alkyl)carbonyl, ($C_{1-18}$-alkyl)oxycarbonyl, arylcarbonyl and aryl-($C_{1-3}$-alkyl)-carbonyl, wherein the alkyl or aryl groups may be mono- or polysubstituted by halogen;
$R^{8a}$, $R^{8b}$, $R^{8c}$, $R^{8d}$ independently of one another has one of the meanings given for the groups $R^6$, $R^{7a}$, $R^{7b}$, $R^{7c}$, or denote a benzyl or allyl group or a $R^aR^bR^c$Si group or a ketal or acetal group, while in each case two adjacent groups $R^{8a}$, $R^{8b}$, $R^{8c}$, $R^{8d}$ may form a cyclic silyl ketal, ketal or acetal group or may form, with two oxygen atoms of the pyranose ring, a substituted 2,3-oxydioxane ring, particularly a 2,3-dimethyl-2,3-di($C_{1-3}$-alkoxy)-1,4-dioxane ring, and while alkyl, aryl and/or benzyl groups may be mono- or polysubstituted by halogen or $C_{1-3}$-alkoxy, and while benzyl groups may also be substituted by a di-($C_{1-3}$-alkyl)amino group; and $R^a$, $R^b$, $R^c$ independently of one another denote $C_{1-4}$-alkyl, aryl or aryl-$C_{1-3}$-alkyl, while the alkyl or aryl groups may be mono- or polysubstituted by halogen;

while by the aryl groups mentioned in the definition of the above groups are meant phenyl or naphthyl groups, preferably phenyl groups;

and $R^2$ to $R^6$, $R^{7a}$, $R^{7b}$, $R^{7c}$ are defined as hereinbefore and hereinafter, wherein an organometallic compound (V) which may be obtained by halogen-metal exchange or by inserting a metal in the carbon-halogen bond of a halogen-benzylbenzene compound of general formula IV

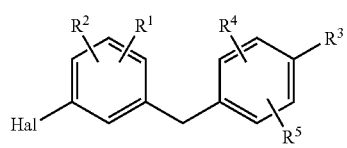

wherein Hal denotes Cl, Br and I and $R^1$ denotes CN, Cl or Br and $R^2$ to $R^5$ are defined as hereinbefore and hereinafter, and optionally subsequent transmetallation, is added to a gluconolactone of general formula VI

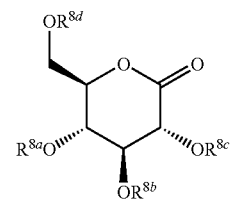

wherein $R^{8a}$, $R^{8b}$, $R^{8c}$, $R^{8d}$ are defined as hereinbefore and hereinafter, and then the resulting adduct is reacted with water or an alcohol R'—OH, while R' denotes optionally substituted $C_{1-4}$-alkyl, in the presence of an acid, such as for example methanesulfonic acid, sulfuric acid, hydrochloric acid, acetic acid or ammonium chloride, and optionally the product obtained in the reaction with water wherein R' denotes H is converted, in a subsequent reaction, with an alcohol in the presence of an acid to yield the alkoxy derivative or with an acylating agent, such as for example the corresponding acid chloride or anhydride, into the product of formula II wherein R' denotes ($C_{1-18}$-alkyl)carbonyl, ($C_{1-18}$-alkyl)oxycarbonyl, arylcarbonyl or aryl-($C_{1-3}$-alkyl)-carbonyl, which may be substituted as specified.

The intermediate products listed, particularly those of formula IV, formula II and formula III, are also a subject of this invention.

DETAILED DESCRIPTION OF THE INVENTION

Unless otherwise stated, the groups, residues and substituents, particularly $R^2$ to $R^5$, L1, L2, $R^6$, $R^{7a}$, $R^{7b}$, $R^{7c}$, $R^{8a}$, $R^{8b}$, $R^{8c}$, $R^{8d}$, are defined as above and hereinafter.

If residues, substituents or groups occur several times in a compound, as for example L1 and L2, they may have the same or different meanings.

Some preferred meanings of individual groups and substituents of the compounds according to the invention will be given hereinafter.

Preferred compounds according to the present invention can be described by the formulae I.1 to I.4:

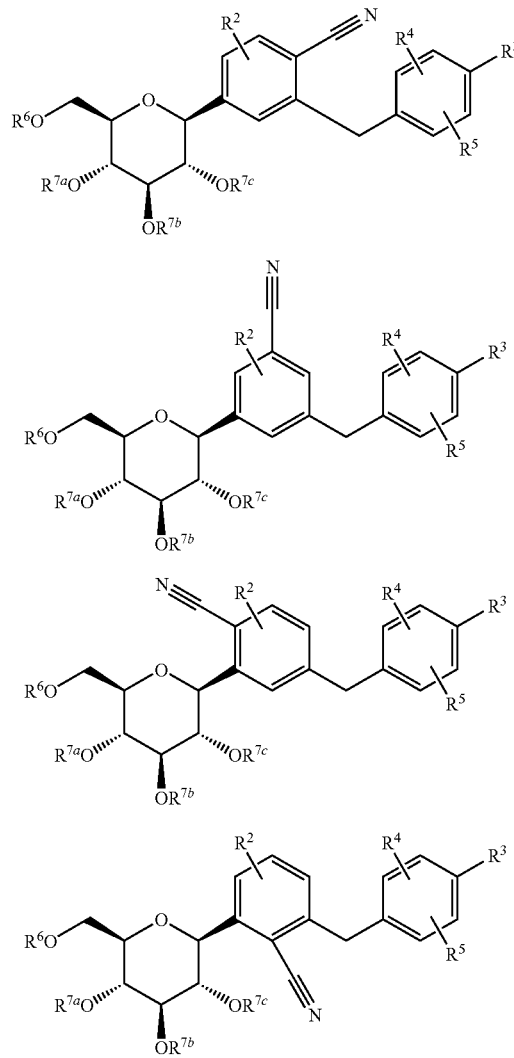

The compounds that bear the cyano group on the central aromatic adjacent to the benzyl group and opposite to the glucose moiety as displayed in the formula I.1 are particularly preferred.

The group $R^2$ preferably denotes fluorine, chlorine, bromine, hydroxy, cyano, $C_{1-4}$-alkyl, $C_{1-4}$-alkyloxy, $C_{3-7}$-cycloalkyl, $C_{3-7}$-cycloalkyloxy or $C_{1-3}$-alkylsulfanyl, while in a $C_{5-6}$-cycloalkyl ring a methylene group may be replaced by O, and wherein any alkyl group or cycloalkyl ring may be mono- or poly-fluorinated and/or mono- or disubstituted with identical or different substituents L2.

Particularly preferred meanings of $R^2$ are chlorine, bromine, methyl, ethyl, cyano, hydroxy, methoxy, ethoxy, isopropoxy, cyclopropyl, cyclobutyl, cyclopentyl, cyclopropyloxy, cyclobutyloxy, cyclopentyloxy, tetrahydrofuran-3-yloxy, tetrahydropyranyloxy, methylsulfanyl, ethylsulfanyl; particularly methyl, ethyl, hydroxy, methoxy, ethoxy, isopropoxy, cyclopropyl, cyclobutyloxy, ((3S)-tetrahydrofuran-3-yl)oxy, ((3R)-tetrahydrofuran-3-yl)oxy, methylsulfanyl and cyano. Most preferably $R^2$ denotes methyl, hydroxy or methoxy.

Preferred meanings of the group $R^3$ are chlorine, bromine, iodine, $C_{1-4}$-alkyl, $C_{3-7}$-cycloalkyl, hydroxyl, $C_{1-4}$-alkyloxy, $C_{3-7}$-cycloalkyloxy, $C_{1-4}$-alkylsulfanyl, $C_{3-7}$-cycloalkylsulfanyl, while in a $C_{5-6}$-cycloalkyl ring a methylene group may be replaced by O, and wherein any alkyl group and cycloalkyl ring may be mono- or polyfluorinated and/or mono- or disubstituted with identical or different substituents L2.

More preferred meanings of the group $R^3$ are chlorine, bromine, methyl, ethyl, propyl, isopropyl, cyclopropyl, butyl, sec-butyl, iso-butyl, tert-butyl, difluoromethyl, trifluoromethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2-methoxy-ethyl, 2-ethoxy-ethyl, hydroxyl, methoxy, ethoxy, isopropoxy, difluoromethoxy, trifluoromethoxy, cyclobutoxy, cyclopentoxy, cyclohexyloxy, (S)-tetrahydrofuran-3-yloxy, (R)-tetrahydrofuran-3-yloxy, tetrahydropyran-4-yloxy, methylsulfanyl and ethylsulfanyl.

Even more preferably $R^3$ denotes methyl, ethyl, n-propyl, isopropyl, cyclopropyl, methoxy, ethoxy, isopropoxy, methylsulfanyl or ethylsulfanyl, in particular ethyl or cyclopropyl.

Preferred meanings of the group $R^4$ are hydrogen and fluorine, particularly hydrogen.

Preferred meanings of the group $R^5$ are hydrogen and fluorine, particularly hydrogen.

Preferred meanings of the group L1 independently of one another are selected from among fluorine, chlorine, bromine, cyano, hydroxy, $C_{1-3}$-alkyl, difluoromethyl, trifluoromethyl, $C_{1-3}$-alkoxy, difluoromethoxy, trifluoromethoxy and di($C_{1-3}$-alkyl)-amino.

Even more preferred meanings of the group L1 are selected from fluorine, chlorine, hydroxy, trifluoromethyl, ethyl, methoxy, ethoxy and dimethylamino, particularly methyl, ethyl, methoxy, ethoxy and dimethylamino.

Preferred meanings of the group L2 independently of one another are selected from among fluorine, hydroxy, hydroxy-$C_{1-4}$-alkyl, $C_{1-4}$-alkoxy, $C_{1-4}$-alkoxy-$C_{1-4}$-alkyl, $C_{1-4}$-alkyl, trifluoromethyl, $C_{1-4}$-alkyl-carbonylamino, hydroxycarbonyl and $C_{1-4}$-alkoxycarbonyl.

Even more preferred meanings of the group L2 are selected from fluorine, hydroxy, hydroxy-$C_{1-4}$-alkyl, $C_{1-4}$-alkoxy, $C_{1-4}$-alkoxy-$C_{1-4}$-alkyl, $C_{1-4}$-alkyl, hydroxycarbonyl and $C_{1-4}$-alkoxy-carbonyl; particularly hydroxy, hydroxymethyl, methoxymethyl, methoxy, methyl, hydroxycarbonyl, methoxycarbonyl and ethoxycarbonyl.

The group $R^6$ preferably denotes according to the invention hydrogen, ($C_{1-8}$-alkyl)oxy-carbonyl, $C_{1-8}$-alkylcarbonyl or benzoyl, particularly hydrogen or ($C_{1-6}$-alkyl)oxycarbonyl or $C_{1-6}$-alkylcarbonyl, particularly preferably hydrogen, methylcarbonyl, methoxycarbonyl or ethoxycarbonyl, most particularly preferably hydrogen.

The substituents $R^{7a}$, $R^{7b}$, $R^{7c}$ preferably represent independently of one another hydrogen, ($C_{1-8}$-alkyl)oxycarbonyl, ($C_{1-18}$-alkyl)carbonyl or benzoyl, particularly hydrogen, ($C_{1-6}$-alkyl)oxy-carbonyl or ($C_{1-8}$-alkyl)carbonyl, particularly preferably hydrogen, methoxycarbonyl, ethoxy-carbonyl, methylcarbonyl or ethylcarbonyl. Most particularly preferably $R^{7a}$, $R^{7b}$ and $R^{7c}$ represent hydrogen.

The compounds of formula I wherein $R^6$, $R^{7a}$, $R^{7b}$ and $R^{7c}$ according to the invention have a meaning other than hydrogen, for example $C_{1-8}$-alkylcarbonyl, are preferably suitable as intermediate products for the synthesis of compounds of formula I wherein $R^6$, $R^{7a}$, $R^{7b}$ and $R^{7c}$ denote hydrogen.

Particularly preferred compounds of general formula I are selected from among formulae I.1a to I.1c, particularly I.1a and I.1b:

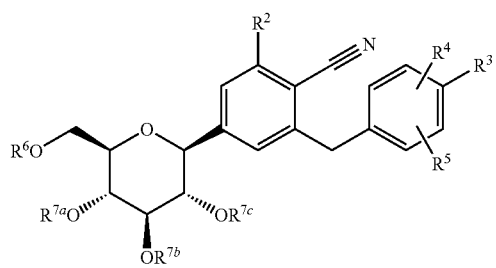

I.1a

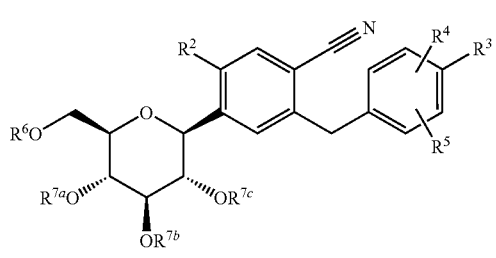

I.1b

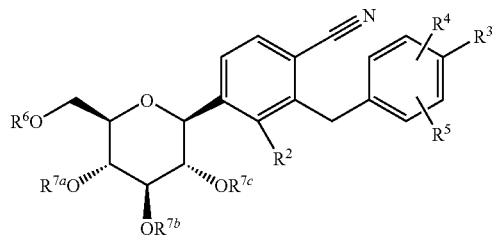

I.1c while the groups $R^2$ to $R^6$ and $R^{7a}$, $R^{7b}$, $R^{7c}$ have one of the meanings given previously, particularly have one of the given meanings specified as being preferred; and particularly $R^2$ denotes fluorine, chlorine, bromine, cyano, $C_{1-4}$-alkyl, hydroxy, $C_{1-4}$-alkyloxy, $C_{3-7}$-cycloalkyl, $C_{3-7}$-cycloalkyloxy or $C_{1-3}$-alkylsulfanyl, while in a $C_{5-6}$-cycloalkyl ring a methylene group may be replaced by O, and wherein any alkyl group and cycloalkyl ring may be mono- or polyfluorinated and/or mono- or disubstituted with identical or different substituents L2; even more preferably $R^2$ denotes chlorine, bromine, methyl, ethyl, cyano, hydroxy, methoxy, ethoxy, isopropoxy, cyclopropyl, cyclobutyl, cyclopentyl, cyclopropyloxy, cyclobutyloxy, cyclopentyloxy, tetrahydrofuran-3-yloxy, tetrahydropyranyloxy, methylsulfanyl, ethylsulfanyl; most preferably $R^2$ denotes methyl, ethyl, hydroxy, methoxy, ethoxy, isopropoxy, cyclopropyl or cyclobutyloxy; and $R^3$ denotes chlorine, bromine, iodine, $C_{1-4}$-alkyl, $C_{3-7}$-cycloalkyl, hydroxyl, $C_{1-4}$-alkyloxy, $C_{3-7}$-cycloalkyloxy, $C_{1-4}$-alkylsulfanyl, $C_{3-7}$-cycloalkylsulfanyl, while in a $C_{5-6}$-cycloalkyl ring a methylene group may be replaced by O; and wherein any alkyl group and cycloalkyl ring may be mono- or polyfluorinated and/or mono- or disubstituted with identical or different substituents L2; even more preferably $R^3$ denotes chlorine, bromine, methyl, ethyl, propyl, isopropyl, cyclopropyl, butyl, sec-butyl, iso-butyl, tert-butyl, difluoromethyl, trifluoromethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2-methoxy-ethyl, 2-ethoxy-ethyl, hydroxyl, methoxy, ethoxy, isopropoxy, difluoromethoxy, trifluoromethoxy, cyclobutoxy, cyclopentoxy, cyclohexyloxy, (S)-tetrahydrofuran-3-yloxy, (R)-tetrahydrofuran-3-yloxy, tetrahydropyran-4-yloxy, methylsulfanyl and ethylsulfanyl; most preferably $R^3$ denotes methyl, ethyl, n-propyl, isopropyl, cyclopropyl, methoxy, ethoxy, isopropoxy, methylsulfanyl or ethylsulfanyl; and $R^4$ denotes hydrogen or fluorine, particularly hydrogen; and $R^5$ denotes hydrogen or fluorine, particularly hydrogen; and L2 independently of one another are selected from among fluorine, hydroxy, hydroxy-$C_{1-4}$-alkyl, $C_{1-4}$-alkoxy, $C_{1-4}$-alkoxy-$C_{1-4}$-alkyl, $C_{1-4}$-alkyl, trifluoromethyl, $C_{1-4}$-alkylcarbonylamino, hydroxycarbonyl and $C_{1-4}$-alkyloxycarbonyl; particularly hydroxy, hydroxymethyl, methoxymethyl, methoxy, methyl, hydroxycarbonyl, methoxycarbonyl and ethoxycarbonyl; and $R^6$ denotes hydrogen, ($C_{1-6}$-alkyl)oxycarbonyl, ($C_{1-6}$-alkyl)carbonyl or benzoyl, particularly hydrogen, methylcarbonyl, methoxycarbonyl or ethoxycarbonyl, most particularly preferably hydrogen; and $R^{7a}$, $R^{7b}$, $R^{7c}$ independently of one another represent hydrogen, ($C_{1-6}$-alkyl)oxycarbonyl, ($C_{1-8}$-alkyl)carbonyl or benzoyl, particularly hydrogen, methoxycarbonyl, ethoxycarbonyl, methylcarbonyl or ethylcarbonyl, particularly preferably hydrogen;

including the tautomers, the stereoisomers, the mixtures thereof and the salts thereof.

The compounds of general formula I specified in the experimental section that follows, and the derivatives thereof, wherein $R^6$ has a meaning according to the invention other than hydrogen, particularly wherein $R^6$ denotes acetyl, ethoxycarbonyl or methoxycarbonyl, including the tautomers, the stereoisomers thereof and the mixtures thereof, are preferred according to another variant of this invention.

In the processes according to the invention the groups $R^2$ to $R^5$ preferably have the meanings specified hereinbefore as being preferred. Moreover R' preferably denotes H, $C_{1-3}$-alkyl or benzyl, particularly H, ethyl or methyl. The groups $R^{8a}$, $R^{8b}$, $R^{8c}$ and $R^{8d}$ independently of one another preferably denote H, $C_{1-4}$-alkylcarbonyl or benzyl, particularly H, methylcarbonyl, ethylcarbonyl or benzyl.

The invention also relates to compounds of general formula IV

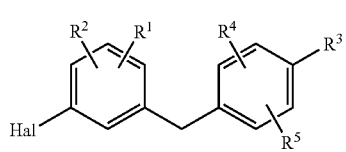

IV wherein Hal denotes chlorine, bromine or iodine, $R^1$ denotes cyano, chlorine or bromine, in particular cyano, and the groups $R^2$ to $R^5$ are as hereinbefore defined, as intermediate products or starting materials in the synthesis of the compounds according to the invention. Particularly preferably, the groups $R^2$ to $R^5$ have the meanings given following formula I.1a.

The invention also relates to compounds of general formula II

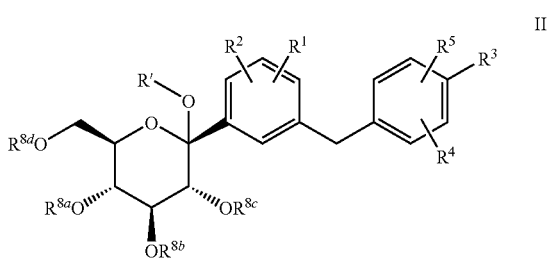

wherein R', $R^{8a}$, $R^{8b}$, $R^{8c}$, $R^{8d}$ and $R^1$ to $R^5$ are defined as hereinbefore and hereinafter; particularly wherein R' denotes H, $C_{1-3}$-alkyl or benzyl, particularly H, ethyl or methyl; $R^1$ denotes cyano, chlorine or bromine, particularly cyano or bromine; and the groups $R^{8a}$, $R^{8b}$, $R^{8c}$ and $R^{8d}$ independently of one another represent H, $C_{1-4}$-alkylcarbonyl, allyl or benzyl, particularly H, methylcarbonyl, ethylcarbonyl or benzyl and the groups $R^2$ to $R^5$ are as hereinbefore defined. These compounds may serve as intermediate products or starting materials in the synthesis of the compounds according to the invention. Particularly preferably the groups $R^2$ to $R^5$ have the meanings given following formulae I.1a to Ic. Some terms used above and hereinafter to describe the compounds according to the invention will now be defined more closely.

The term halogen denotes an atom selected from the group consisting of F, Cl, Br and I.

The term $C_{1-n}$-alkyl, wherein n may have a value of 2 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc. Unless otherwise stated alkynyl groups are connected to the remainder of the molecule via the C atom in position 1. Therefore terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclodecyl, decalinyl, bicyclo[3.2.1]octyl, spiro[4.5]decyl, norpinyl, norbonyl, norcaryl, adamantyl, etc. Preferably the term $C_{3-n}$-cycloalkyl denotes saturated monocyclic groups.

The term $C_{5-n}$-cycloalkenyl denotes a $C_{5-n}$-cycloalkyl group which is as hereinbefore defined and additionally has at least one unsaturated C=C double bond.

The term $C_{3-n}$-cycloalkylcarbonyl denotes a $C_{3-n}$-cycloalkyl-C(=O) group wherein $C_{3-n}$-cycloalkyl is as hereinbefore defined.

The term tri-($C_{1-4}$-alkyl)silyl comprises silyl groups which have identical or two or three different alkyl groups.

The term di-($C_{1-3}$-alkyl)amino comprises amino groups which have identical or two different $C_{1-3}$-alkyl groups.

The term aryl preferably denotes naphthyl or phenyl, more preferably phenyl.

The term heteroaryl denotes a 5- or 6-membered monocyclic aromatic ring possessing one to four identical or different heteroatoms selected from the group comprising N, O and S. Heteroaryl denotes preferably a pyrrolyl, furanyl, thienyl, pyridyl or tetrazolyl group, or a pyrrolyl, furanyl, thienyl or pyridyl group wherein one or two methine groups are replaced in each case by a nitrogen atom.

The nomenclature in structural formulas used above and hereinafter, in which a bond of a substituent of a cyclic group, as e.g. a phenyl ring, is shown towards the centre of the cyclic group, denotes, unless otherwise stated, that this substituent may be bound to any free position of the cyclic group bearing an H atom.

The compounds according to the invention may be obtained using methods of synthesis known in principle. Preferably the compounds are obtained by the following methods according to the invention which are described in more detail hereinafter.

The glucose derivatives of formula II according to the invention may be synthesised from D-gluconolactone or a derivative thereof by adding the desired benzylbenzene compound in the form of an organometallic compound (Scheme 1).

Scheme 1: Addition of an Organometal Compound to a Gluconolactone

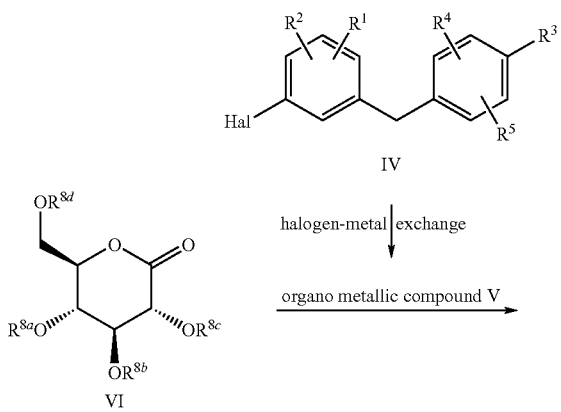

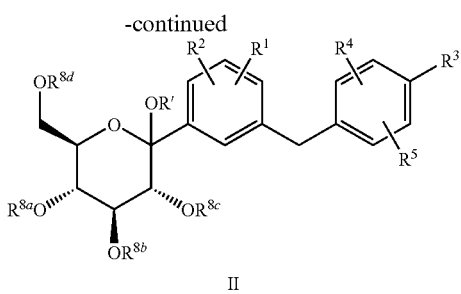

II

The reaction according to Scheme 1 is preferably carried out starting from a halogenated benzylbenzene compound of general formula IV, wherein Hal denotes chlorine, bromine, or iodine. $R^1$ in Scheme 1 denotes cyano or a group that may be subsequently converted to a cyano group such as chlorine, bromine, carboxy, carboxylic ester, carboxamide or a derivative thereof, a boron or silyl group, a protected or masked aldehyde function such as e.g. acetal or thiazole, or a protected or masked amino functionality such as e.g. nitro. The Grignard or lithium reagent of benzylbenzene (V) may be prepared from the corresponding chlorinated, brominated or iodinated benzylbenzene IV either via a so-called halogen-metal exchange reaction or by inserting the metal into the carbon-halogen bond. The halogen-metal exchange to synthesize the corresponding lithium compound V may be carried out for example with an organolithium compound such as e.g. n-, sec- or tert-butyllithium. The analogous magnesium compound may also be generated by a halogen-metal exchange with a suitable Grignard reagent such as e.g. isopropyl- or sec-butylmagnesium bromide or chloride or diisopropyl- or di-sec-butylmagnesium without or in the presence of an additional salt such as e.g. lithium chloride that may accelerate the metalation process; the specific transmetalating organomagnesium compound may also be generated in situ from suitable precursors (see e.g. *Angew. Chem.* 2004, 116, 3396-3399 and *Angew. Chem.* 2006, 118, 165-169 and references quoted therein). In addition, ate complexes of organomagnesium compounds resulting from combining e.g. butylmagnesium chloride or bromide or isopropylmagnesium chloride or bromide and butyllithium, may be employed as well (see e.g. *Angew. Chem.* 2000, 112, 2594-2596 and *Tetrahedron Lett.* 2001, 42, 4841-4844 and references quoted therein). The halogen-metal exchange reactions are preferably carried out between 40° C. and −100° C., particularly preferably between 10° C. and −80° C., in an inert solvent or mixtures thereof, such as for example diethylether, dioxane, tetrahydrofuran, toluene, hexane, dimethylsulfoxide, dichloromethane or mixtures thereof. The magnesium or lithium derivatized compounds thus obtained may optionally be transmetalated with metal salts such as e.g. cerium trichloride, zinc chloride or bromide, indium chloride or bromide, to form alternative organometal compounds (V) suitable for addition. Alternatively, the organometal compound V may also be prepared by inserting a metal into the carbon-halogen bond of the haloaromatic compound IV. Lithium or magnesium are suitable elemental metals for this transformation. The insertion can be achieved in solvents such as e.g. diethylether, dioxane, tetrahydrofuran, toluene, hexane, dimethylsulfoxide and mixtures thereof at temperatures ranging from −80 to 100° C., preferably at −70 to 40° C. In cases in which no spontaneous reaction takes place prior activation of the metal might be necessary such as e.g. treatment with 1,2-dibromoethane, iodine, trimethylsilylchloride, acetic acid, hydrochloric acid and/or sonication. The addition of the organometal compound V to gluconolactone or derivatives thereof (VI) is preferably carried out at temperatures between 40° C. and −100° C., particularly preferably at 0 to −80° C., in an inert solvent or mixtures thereof, to obtain the compound of formula II. All foregoing reactions may be performed in air though execution under inert gas atmosphere such as argon and nitrogen is preferred. The metalation and/or coupling reaction may also be carried out in microreactors and/or micromixers which enable high exchange rates; for example analogously to the processes described in WO 2004/076470. Suitable solvents for the addition of the metalated phenyl group V to the appropriately protected gluconolactone VI are e.g. diethylether, dimethoxyethane, benzene, toluene, methylene chloride, hexane, tetrahydrofuran, dioxane, N-methylpyrrolidone and mixtures thereof. The addition reactions may be carried out without any further adjuvants or in the case of sluggishly reacting coupling partners in the presence of a promoter such as e.g. $BF_3$*$OEt_2$ or $Me_3SiCl$ (see M. Schlosser, Organometallics in Synthesis, John Wiley & Sons, Chichester/New York/Brisbane/Toronto/Singapore, 1994). Preferred definitions of the substituents $R^8$ in Scheme 1 are benzyl, substituted benzyl, allyl, trialkylsilyl, particularly preferably trimethylsilyl, triisopropylsilyl, allyl, 4-methoxybenzyl and benzyl. If two adjacent substituents $R^8$ are linked together, these two substituents are preferably part of a benzylideneacetal, 4-methoxybenzylideneacetal, isopropylketal or constitute a dioxane with 2,3-dimethoxy-butylene which is linked via the 2 and 3 positions of the butane with the adjacent oxygen atoms of the pyranose. The group R' preferably denotes hydrogen, $C_{1-4}$-alkyl, $C_{1-4}$-alkylcarbonyl or $C_{1-4}$-alkyloxycarbonyl, particularly preferably hydrogen, methyl or ethyl. The group R' is introduced after the addition of the organometallic compound V or a derivative thereof to the gluconolactone VI. If R' equals hydrogen or $C_{1-4}$-alkyl the reaction solution is treated with an alcohol such as e.g. methanol or ethanol or water in the presence of an acid such as e.g. acetic acid, methanesulfonic acid, toluenesulfonic acid, sulfuric acid, trifluoroacetic acid, or hydrochloric acid. R' may also be attached after preparation of the hydrogen compound II by reacting the compound with an alcohol under acidic conditions. During installing R' the protective groups $R^8$ may be cleaved if labile under the reaction conditions employed resulting in the corresponding protonated compound, i.e. compound II in which $R^8$ equals H.

The synthesis of haloaromatic compound of formula IV may be carried out using standard transformations in organic chemistry or at least methods known from the specialist literature in organic synthesis (see inter alia J. March, Advanced Organic Reactions, Reactions, Mechanisms, and Structure, 4th Edition, John Wiley & Sons, Chichester/New York/Brisbane/Toronto/Singapore, 1992 and literature cited therein). More specifically, the use of transition metals and organo metal compounds for the synthesis of aromatic compounds has been detailed in different monographs (see e.g. L. Brandsma, S. F. Vasilevsky, H. D. Verkruijsse, Application of Transition Metal Catalysts in Organic Synthesis, Springer-Verlag, Berlin/Heidelberg, 1998; M. Schlosser, Organometallics in Synthesis, John Wiley & Sons, Chichester/New York/Brisbane/Toronto/Singapore, 1994; P. J. Stang, F. Diederich, *Metal-Catalyzed Cross-Coupling Reactions*, Wiley-VCH, Weinheim, 1997 and references quoted therein). The synthesis strategies described in the following provide a demonstration of this, by way of example. In addition, the aglycon part may also be assembled with the pyranose moiety already present using the same synthetic approaches.

Scheme 2: Synthesis of the Diarylketone Fragment

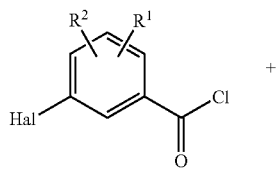

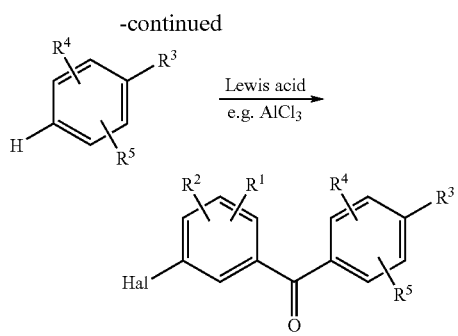

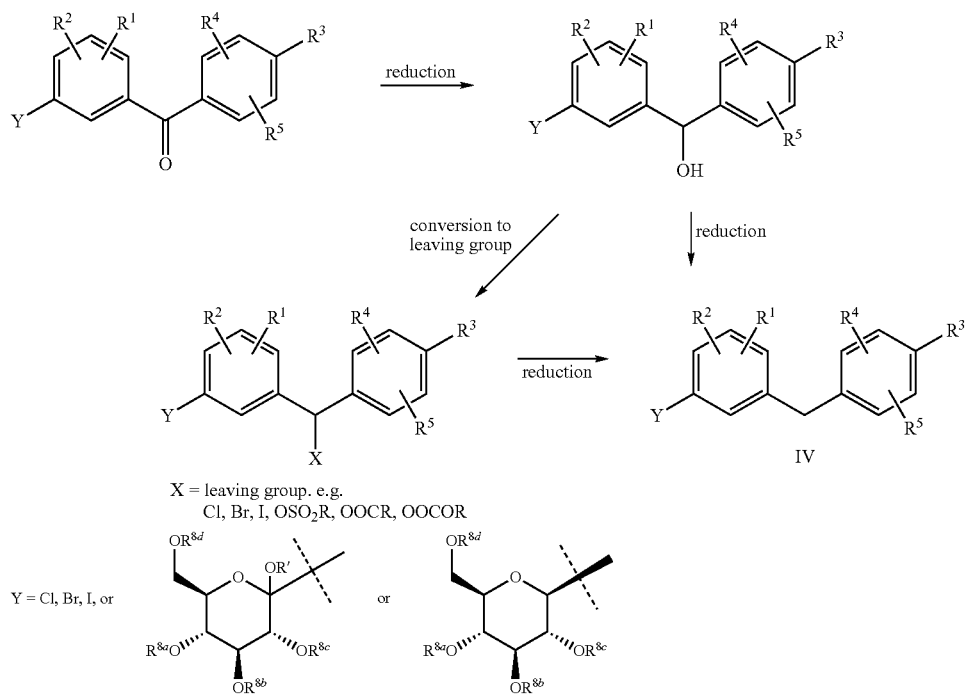

Scheme 2 shows the preparation of a precursor compound that may serve for the synthesis of the haloaromatic compound of formula IV starting from a benzoylchloride and a second aromatic group applying Friedel-Crafts acylation conditions or variations thereof. $R^1$ in Scheme 2 denotes cyano or a group that may be subsequently converted to a cyano group such as chlorine, bromine, carboxy, carboxylic ester, carboxamide or a derivative thereof, a protected or masked aldehyde function such as e.g. thioacetal or thiazole, or a protected or masked amino functionality such as e.g. nitro. This classic reaction has a wide substrate scope and is commonly carried out in the presence of a catalyst which is used in catalytic or stoichiometric amounts, such as e.g. $AlCl_3$, $FeCl_3$, iodine, iron, $ZnCl_2$, sulphuric acid, or trifluoromethanesulphonic acid. Instead of the benzoyl chloride the corresponding carboxylic acid, anhydride, ester or benzonitrile may be used as well. The reactions are preferentially carried out in chlorinated hydrocarbons such as e.g. dichloromethane and 1,2-dichloroethane at temperatures from −30 to 120° C., preferably at 30 to 100° C. However, solvent-free reactions or reactions in a microwave oven are also possible.

In Scheme 3 the substituent R denotes $C_{1-3}$-alkyl or aryl and $R^1$ cyano or a group that may be subsequently converted to a cyano group such as chlorine, bromine, carboxy, carboxylic ester, carboxamide or a derivative thereof, a boron or silyl group, a protected or masked aldehyde function such as e.g. acetal or thiazole, or a protected or masked amino function such as e.g. nitro. Starting from the diarylketone or diarylmethanol the diarylmethane is accessible in one or two reaction steps. The diarylketone may be reduced to the diarylmethane in two steps via the corresponding diphenylmethanol or in one step. In the two-step variant the ketone is reduced with a reducing agent such as for example a metal hydride such as e.g. $NaBH_4$, $LiAlH_4$ or $iBu_2AlH$ to form the alcohol. The resulting alcohol can be converted in the presence of a Lewis acid such as for example $BF_3*OEt_2$, $InCl_3$ or $AlCl_3$ or Brønsted acid such as for example hydrochloric acid, sulfuric acid, trifluoroacetic acid, or acetic acid with a reducing agent such as e.g. $Et_3SiH$, $NaBH_4$, or $Ph_2SiClH$ to the desired diphenylmethane. The one-step process starting from the ketone to obtain the diphenylmethane may be carried out e.g. with a silane such as e.g. $Et_3SiH$, a borohydride such as e.g. $NaBH_4$ or an aluminum hydride such as $LiAlH_4$ in the presence of a Lewis or Brønsted acid such as for example BF$_3$*OEt$_2$, tris(pentafluorophenyl)borane, trifluoroacetic acid, hydrochloric acid, aluminum chloride or InCl$_3$. The reactions are preferably carried out in solvents such as e.g. halogenated hydrocarbons such as dichloromethane, toluene, acetonitrile, or mixtures thereof at temperatures of −30 to 150° C., preferably at 20 to 100° C. Reductions with hydrogen in the presence of a transition metal catalyst such as e.g. Pd on charcoal are another possible method of synthesis. Reductions according to Wolff-Kishner or variants thereof are also possible. The ketone is firstly converted with hydrazine or a derivative thereof, such as e.g. 1,2-bis(tert-butyldimethylsilyl)hydrazine, into the hydrazone which breaks down under strongly basic reaction conditions and heating to form the diphenylmethane and nitrogen. The reaction may be carried out in one reaction step or after isolation of the hydrazone or a derivative thereof in two separate reaction steps. Suitable bases include e.g. KOH, NaOH or KOtBu in solvents such as e.g. ethyleneglycol, toluene, DMSO, 2-(2-butoxyethoxy) ethanol or tert-butanol; solvent-free reactions are also possible. The reactions may be carried out at temperatures between 20 to 250° C., preferably between 80 to 200° C. An alternative to the basic conditions of the Wolff-Kishner reduction is the Clemmensen reduction which takes place under acidic conditions, which may also be used here. The alcohol function in diarylmethanol may also first be transformed into a better leaving group such as e.g. chloride, bromide, iodide, acetate, carbonate, phosphate, or sulfate; the subsequent reduction step to form the diarylmethane is widely described in the organic chemistry literature.

Scheme 4: Synthesis of Diarylmethane Unit and Possible Precursor Compounds thereof

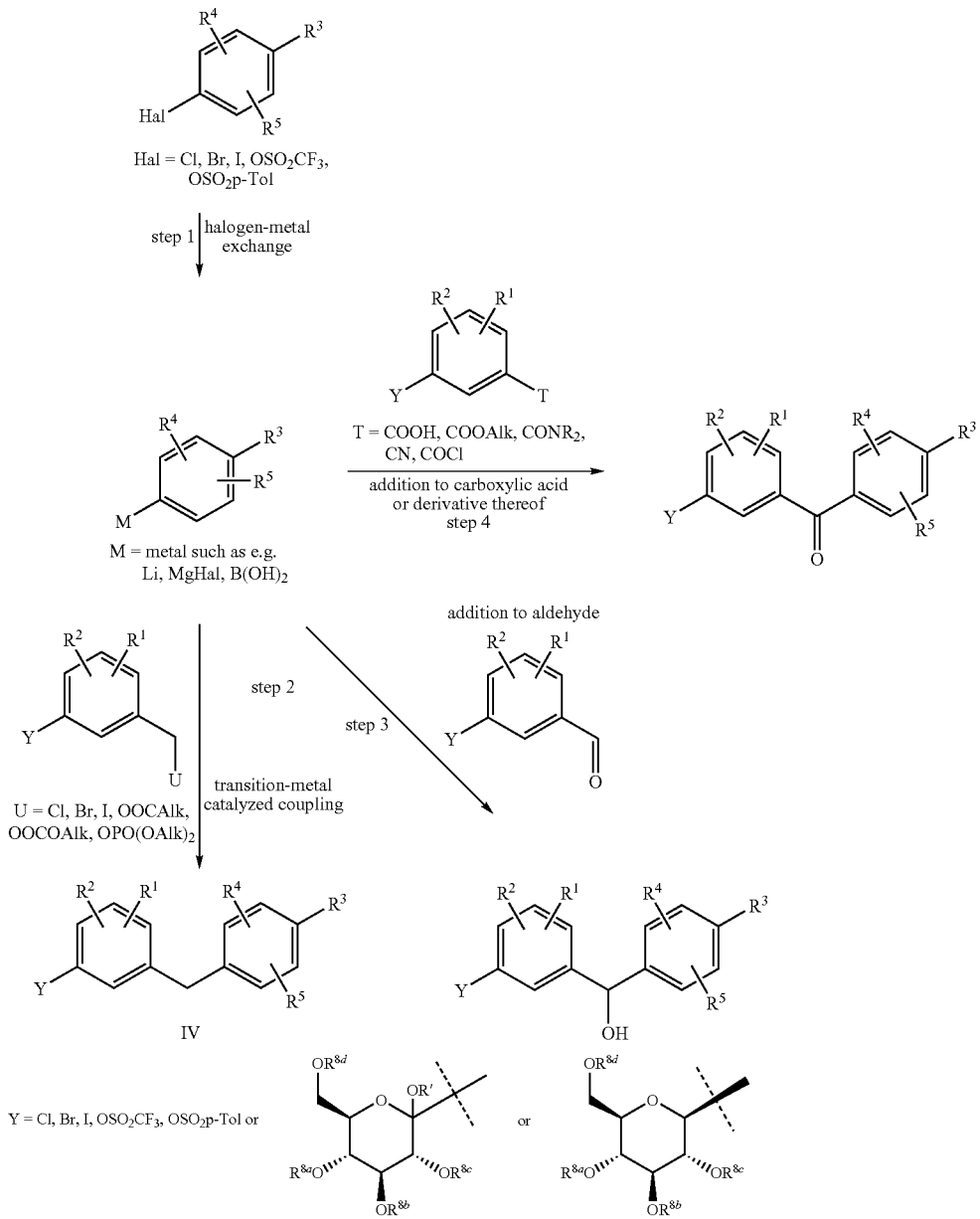

In Scheme 4 $R^1$ denotes cyano or a group that may be subsequently converted to a cyano group such as chlorine, bromine, carboxy, carboxylic ester, carboxamide or a derivative thereof, a boron or silyl group, a protected or masked aldehyde function such as e.g. acetal or thiazole, or a protected or masked amino function such as e.g. nitro. The term "Alk" denotes $C_{1-3}$-alkyl and each substituent R is independently selected from each other from the group consisting of H, $C_{1-3}$-alkyl and $C_{1-3}$-alkoxy. Scheme 4 delineates the synthesis of diarylmethanes and possible precursor compounds thereof starting from a metalated phenyl group. Lithium or magnesium substituted aromatic compounds may be synthesized from chlorinated, brominated, or iodinated aromatics by a halogen-metal exchange reaction with e.g. butyllithium, isopropylmagnesium halogenide, or diisopropylmagnesium or by insertion of the elemental metal into the halogen-carbon bond. The corresponding boron substituted compound such as e.g. boronic acid, boronic acid ester, or dialkylarylborane, is accessible from these metalated phenyl groups by reaction with a boron electrophile such as e.g. boronic acid ester or a derivative thereof. In addition, the borylated aromatic compound may also be prepared from the corresponding halogenated or pseudohalogenated precursor and a diboron or borane compound through a transition metal, e.g. palladium, catalyzed reaction (see e.g. *Tetrahedron Lett.* 2003, p. 4895-4898 and references quoted therein). The lithium or magnesium substituted phenyl compounds add to benzaldehydes (step 3) and benzoic acids or derivatives thereof (step 4) such as benzoic acid esters, benzamides such as e.g. of the Weinreb type, benzonitriles, or benzoyl chlorides. These reactions may principally be conducted without an additional transition metal catalyst or transmetalation to another metal such as e.g. cerium, indium or zinc; sometimes the use of one of the latter alternatives is advantageous. Aryl boronic acids can be added to benzaldehydes by means of a rhodium catalyst furnishing the respective diarylmethanol (see e.g. *Adv. Synth. Catal.* 2001, p. 343-350 and references quoted therein). Moreover, arylboronic acids, esters thereof, dialkylarylboranes, or aryltrifluoroborates may be coupled with benzoyl chlorides mediated by a transition metal such as e.g. palladium, a complex or a salt thereof delivering diarylketones. Metalated phenyl groups can be reacted with benzyl electrophiles such as benzyl chlorides, bromides, or iodides affording diarylmethanes. Lithium or magnesium derivatized phenyl compounds are reacted favorably but not always necessarily in the presence of a transition metal such as e.g. copper, iron, or palladium (see e.g. *Org. Lett.* 2001, 3, 2871-2874 and references quoted therein). Transmetallation from lithium or magnesium to e.g. boron, tin, silicon, or zinc furnishes e.g. the corresponding aromatic boronic acids, stannanes, silanes or zinc compounds, respectively, that may undergo coupling with benzyl electrophiles, e.g. benzyl halogenides, carbonates, phosphates, sulfonates, or carboxylic esters. The reaction is conducted in the presence of a transition metal, e.g. palladium, nickel, rhodium, copper, or iron (see e.g. *Tetrahedron Lett.* 2004, p. 8225-8228 and *Org. Lett.* 2005, p. 4875-4878 and references cited therein).

Scheme 5: Introduction of the Cyano Moiety

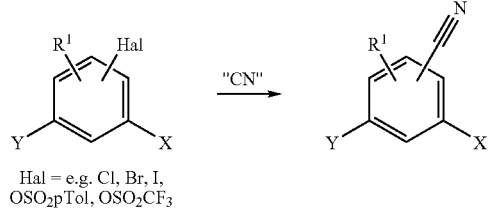

Hal = e.g. Cl, Br, I, OSO$_2$pTol, OSO$_2$CF$_3$

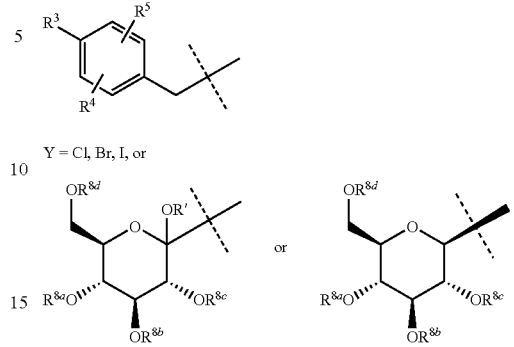

X = e.g. Me, COOH, COOAlk, CH$_2$OH, CH$_2$OAlk, CH$_2$OAr,

Y = Cl, Br, I, or

Scheme 5 displays possible pathways to attach the cyano residue to the central phenyl group at various stages of the synthesis of the target molecules. The cyano group may be introduced via a transition metal mediated coupling reaction of an appropriate cyano source such as e.g. sodium, potassium, zinc or copper cyanide with a halogenated or pseudohalogenated phenyl group. Suitable catalysts may be derived from transition metals such as e.g. palladium, rhodium, nickel, iron or copper that may be used in elemental form such as e.g. palladium on carbon, as salts such as e.g. palladium chloride, bromide or acetate or complexes with e.g. phosphines such as e.g. triphenylphosphine, tri-tert-butylphosphine or dppf or alkenes such as e.g. dibenzylideneacetone. The active catalyst may be generated in situ or prior to the addition to the reaction mixture. Additives such as e.g. zinc as element or salt may be advantageous (see *Tetrahedron Lett.* 2005, 46, 1849-1853 and *Tetrahedron Lett.* 2005, 46, 1815-1818 and references quoted therein). Reacting the corresponding zinc, magnesium or lithium compound, accessible from the chlorinated, brominated or iodinated compound via a halogen metal exchange reaction or by insertion of the respective metal into the halogen bond, with a cyano electrophile such as e.g. p-tolylsulfonyl cyanide, cyanogen bromide or 2-pyridyl cyanate is another viable approach to install the cyano functionality (see e.g. *Synth. Commun.* 1996, 3709-3714 and references quoted therein).

Scheme 6: Introduction of the cyano residue from aldehyde or carboxylic acid derivative

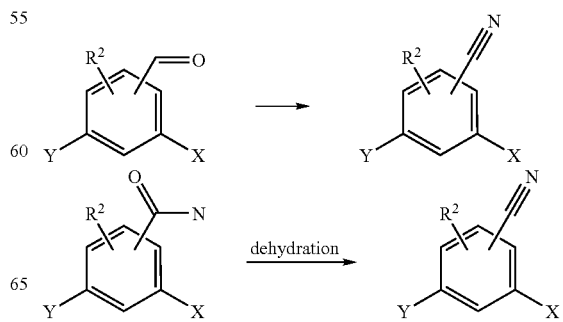

-continued

X = e.g. Me, COOH, COOAlk, CH$_2$OH, CH$_2$OAlk, CH$_2$OAr,

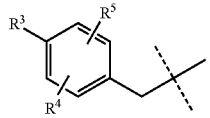

Y = Cl, Br, I, or

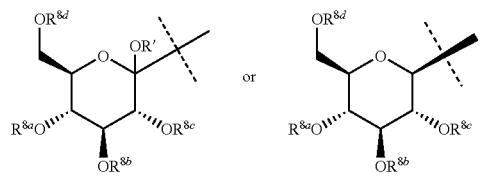

An alternative introduction of the cyano group is the synthesis starting from aldehyde or carboxamide (Scheme 6). The aldehydic function itself can be introduced as such, protected, or masked. Popular protective groups for the aldehyde function are acetals, but other protective groups may be used as well (see T. W. Greene, P. G. M. Wuts, Protective Groups in Organic Synthesis, John Wiley & Sons, Inc., New York, 1999). Suitable masks for the aldehyde function are e.g. olefins and thiazoles. The aldehyde may be converted to the cyano function using e.g. hydroxylamine in combination with e.g. formic acid, concentrated hydrochloric acid, polyphosphoric acid or pyridine-toluene. The intermediate oxime formed under these reaction conditions may be isolated before dehydration to deliver the final product. Alternative hydroxylamine reagents such as e.g. bistrifluoroacetylhydroxylamine and NH$_2$OSO$_3$ may be used as well and afford the nitrile without additional reagents. Further reagents applicable are e.g. NH$_4$PO$_4$H$_2$ and nitropropane in acetic acid, trimethylsilyl azide or S,S-dimethylsulfurdiimide.

Carboxamides may be suitable nitrile precursors, too. The conversion may be carried out with dehydrating agents such as e.g. trifluoroacetic acid anhydride, phosphorous pentoxide, POCl$_3$, CCl$_4$-phosphine combination, Cl$_3$COCl-amine combination, Burgess reagent, Vilsmeyer reagent, SOCl$_2$, or cyanuric chloride. Starting from the corresponding monoalkylated carboxamide, carboxylic acid, ester or carboxylic chloride the formation of the nitrile is also doable in one pot without the isolation of any intermediate.

Scheme 7: Introduction of the cyano residue from aniline precursor

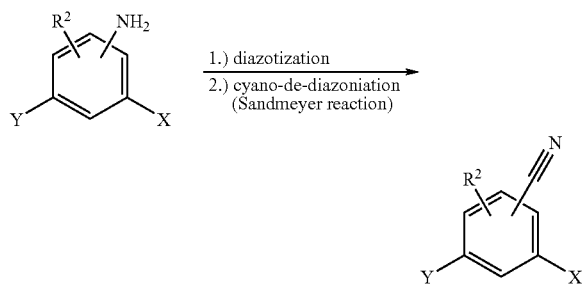

-continued

X = e.g. Me, COOH, COOAlk, CH$_2$OH, CH$_2$OAlk, CH$_2$OAr,

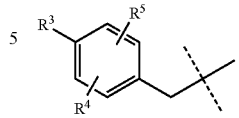

Y = Cl, Br, I, or

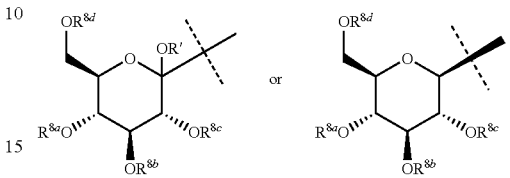

A well established approach to introduce the nitrile function is the so-called Sandmeyer reaction with copper cyanide and the corresponding diazonium compound accessible via diazotization of the respective aniline derivative. The synthesis of diazonium compounds and their subsequent cyano-de-diazoniation has extensively been documented in the organic chemistry literature.

In order to prepare compounds of general formula I, in process a) according to the invention, a compound of general formula II

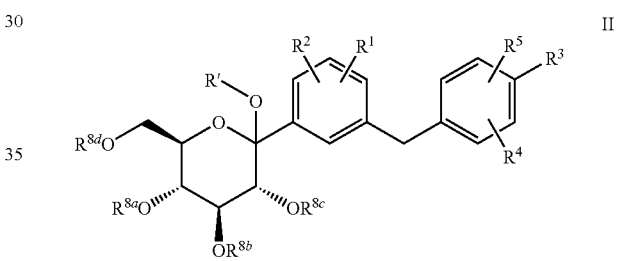

II wherein R', R$^1$ to R$^5$ are as hereinbefore defined and

R$^{8a}$, R$^{8b}$, R$^{8c}$, R$^{8d}$ are as hereinbefore defined and independently of one another represent for example acetyl, pivaloyl, benzoyl, tert-butoxycarbonyl, benzyloxycarbonyl, trialkylsilyl, allyl, benzyl or substituted benzyl or in each case two adjacent groups R$^{8a}$, R$^{8b}$, R$^{8c}$, R$^{8d}$ are combined a benzylideneacetal, diisopropylsilylideneketal or isopropylideneketal or a 2,3-dimethoxy-butylene group which is linked via position 2 and 3 of the butylene group to the oxygen atoms of the pyranose ring and forms with them a substituted dioxane, which may be obtained as hereinbefore described, is reacted with a reducing agent in the presence of a Lewis or Brønsted acid.

Suitable reducing agents for the reaction include for example silanes, such as triethyl-, tripropyl-, triisopropyl- or diphenylsilane, sodium borohydride, sodium cyanoborohydride, zinc borohydride, boranes, lithium aluminium hydride, diisobutylaluminium hydride or samarium iodide. The reductions are carried out without or in the presence of a suitable Brønsted acid, such as e.g. hydrochloric acid, toluenesulphonic acid, trifluoroacetic acid or acetic acid, or Lewis acid, such as e.g. boron trifluoride etherate, trimethylsilyltriflate, titanium tetrachloride, tin tetrachloride, scandium triflate or zinc iodide. Depending on the reducing agent and the acid used the reaction may be carried out in a solvent, such as for example methylene chloride, chloroform, acetonitrile, toluene, hexane, diethyl ether, tetrahydrofuran, dioxane, ethanol, water or mixtures thereof at temperatures between −60° C. and 120° C. One particularly suitable combination of reagents consists for example of triethylsilane and boron trifluoride etherate, which is conveniently used in acetonitrile or dichloromethane at temperatures of −60° C. and 60° C. Moreover, hydrogen may be used in the presence of a transition metal catalyst, such as e.g. palladium on charcoal or Raney nickel, in solvents such as tetrahydrofuran, ethyl acetate, methanol, ethanol, water or acetic acid, for the transformation described.

Alternatively, in order to prepare compounds of general formula I according to process b) according to the invention, in a compound of general formula III

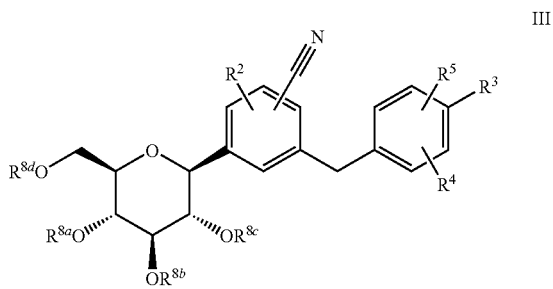

wherein $R^2$ to $R^5$ are as hereinbefore defined and $R^{8a}$ to $R^{8d}$ denote one of the protective groups defined hereinbefore, such as e.g. an acyl, allyl, arylmethyl, acetal, ketal or silyl group, and which may be obtained for example by reduction from the compound of formula II as hereinbefore described, the protective groups are cleaved.

Any acyl protecting group used is cleaved for example hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulfuric acid or in the presence of an alkali metal base such as lithium hydroxide, sodium hydroxide or potassium hydroxide or aprotically, e.g. in the presence of iodotrimethylsilane, at temperatures between 0 and 120° C., preferably at temperatures between 10 and 100° C. A trifluoroacetyl group is preferably cleaved by treating with an acid such as hydrochloric acid, optionally in the presence of a solvent such as acetic acid at temperatures between 50 and 120° C. or by treating with sodium hydroxide solution optionally in the presence of a solvent such as tetrahydrofuran or methanol at temperatures between 0 and 50° C.

Any acetal or ketal protecting group used is cleaved for example hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulfuric acid or aprotically, e.g. in the presence of iodotrimethylsilane, at temperatures between 0 and 120° C., preferably at temperatures between 10 and 100° C.

A trimethylsilyl group is cleaved for example in water, an aqueous solvent mixture or a lower alcohol such as methanol or ethanol in the presence of a base such as lithium hydroxide, sodium hydroxide, potassium carbonate or sodium methoxide. In aqueous or alcoholic solvents, acids such as e.g. hydrochloric acid, trifluoroacetic acid or acetic acid are also suitable. For cleaving in organic solvents, such as for example diethyl ether, tetrahydrofuran or dichloromethane, it is also suitable to use fluoride reagents, such as e.g. tetrabutylammonium fluoride.

A benzyl, methoxybenzyl or benzyloxycarbonyl group is advantageously cleaved hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole. A benzyl group may also be cleaved by boron trichloride or aluminium trichloride in the presence of anisol or pentamethylbenzene.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethylether.

In the reactions described hereinbefore, any reactive groups present such as ethynyl, hydroxy, amino, alkylamino or imino groups may be protected during the reaction by conventional protecting groups which are cleaved again after the reaction.

For example, a protecting group for an ethynyl group may be trialkylsilyl such as e.g. trimethylsilyl and triisopropylsilyl or dialkyl-hydroxymethyl such as e.g. 2-hydroxyisoprop-2-yl.

For example, a protecting group for a hydroxy group may be a methyl, methoxymethyl, trimethylsilyl, acetyl, trityl, benzyl or tetrahydropyranyl group.

Protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyl-tartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulfuric acid, methanesulfonic acid, phosphoric acid, fumaric acid, succinic acid, lactic acid, citric acid, tartaric acid or maleic acid.

Moreover, the compounds obtained may be converted into mixtures, for example 1:1 or 1:2 mixtures with amino acids, particularly with alpha-amino acids such as proline or phenylalanine, which may have particularly favourable properties such as a high crystallinity.

The compounds according to the invention are advantageously also obtainable using the methods described in the examples that follow, which may also be combined for this purpose with methods known to the skilled man from the literature, for example the methods described in WO 98/31697, WO 01/27128, WO 02/083066, WO 03/099836, WO 2004/063209, WO 2004/080990, WO 2004/013118, WO 2004/052902, WO 2004/052903, WO 2005/092877, WO 06/010557, WO 06/018150, WO 06/037537, WO 06/089872, WO 2006/064033, WO 2007/093610 and US application US 2003/0114390.

As already mentioned, the compounds of general formula I according to the invention and the physiologically acceptable salts thereof have valuable pharmacological properties, particularly an inhibitory effect on the sodium-dependent glucose cotransporter SGLT, preferably SGLT2.

The biological properties of the new compounds may be investigated as follows:

The ability of the substances to inhibit the SGLT-2 activity may be demonstrated in a test set-up in which a CHO-K1 cell line (ATCC No. CCL 61) or alternatively an HEK293 cell line (ATCC No. CRL-1573), which is stably transfected with an expression vector pZeoSV (Invitrogen, EMBL accession number L36849), which contains the cDNA for the coding sequence of the human sodium glucose cotransporter 2 (Genbank Acc. No. NM_003041) (CHO-hSGLT2 or HEK-hSGLT2). These cell lines transport $^{14}C$-labelled alpha-methyl-glucopyranoside ($^{14}C$-AMG, Amersham) into the interior of the cell in sodium-dependent manner.

The SGLT-2 assay is carried out as follows:

CHO-hSGLT2 cells are cultivated in Ham's F12 Medium (BioWhittaker) with 10% foetal calf serum and 250 µg/ml zeocin (Invitrogen), and HEK293-hSGLT2 cells are cultivated in DMEM medium with 10% foetal calf serum and 250 µg/ml zeocin (Invitrogen). The cells are detached from the culture flasks by washing twice with PBS and subsequently treating with trypsin/EDTA. After the addition of cell culture medium the cells are centrifuged, resuspended in culture medium and counted in a Casy cell counter. Then 40,000 cells per well are seeded into a white, 96-well plate coated with poly-D-lysine and incubated overnight at 37° C., 5% $CO_2$. The cells are washed twice with 250 µl of assay buffer (Hanks Balanced Salt Solution, 137 mM NaCl, 5.4 mM KCl, 2.8 mM $CaCl_2$, 1.2 mM $MgSO_4$ and 10 mM HEPES (pH7.4), 50 µg/ml of gentamycin). 250 µl of assay buffer and 5 µl of test compound are then added to each well and the plate is incubated for a further 15 minutes in the incubator. 5 µl of 10% DMSO are used as the negative control. The reaction is started by adding 5 µl of $^{14}C$-AMG (0.05 µCi) to each well. After 2 hours' incubation at 37° C., 5% $CO_2$, the cells are washed again with 250 µl of PBS (20° C.) and then lysed by the addition of 25 µl of 0.1 N NaOH (5 min. at 37° C.). 200 µl of MicroScint20 (Packard) are added to each well and incubation is continued for a further 20 min at 37° C. After this incubation the radioactivity of the $^{14}C$-AMG absorbed is measured in a Topcount (Packard) using a $^{14}C$ scintillation program.

To determine the selectivity with respect to human SGLT1 an analogous test is set up in which the cDNA for hSGLT1 (Genbank Acc. No. NM000343) instead of hSGLT2 cDNA is expressed in CHO-K1 or HEK293 cells.

The compounds of general formula I according to the invention may for example have EC50 values below 1000 nM, particularly below 200 nM, most preferably below 50 nM.

In view of their ability to inhibit the SGLT activity, the compounds according to the invention and the corresponding pharmaceutically acceptable salts thereof are suitable for the treatment and/or preventative treatment of all those conditions or diseases which may be affected by the inhibition of the SGLT activity, particularly the SGLT-2 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia. These substances are also suitable for preventing beta-cell degeneration such as e.g. apoptosis or necrosis of pancreatic beta cells. The substances are also suitable for improving or restoring the functionality of pancreatic cells, and also of increasing the number and size of pancreatic beta cells. The compounds according to the invention may also be used as diuretics or antihypertensives and are suitable for the prevention and treatment of acute renal failure.

By the administration of a compound according to the invention an abnormal accumulation of fat in the liver may be reduced or inhibited. Therefore according to another aspect of the present invention there is provided a method for preventing, slowing, delaying or treating diseases or conditions attributed to an abnormal accumulation of liver fat in a patient in need thereof characterized in that a compound or a pharmaceutical composition according to the present invention is administered. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver or toxic fatty liver.

In particular, the compounds according to the invention, including the physiologically acceptable salts thereof, are suitable for the prevention or treatment of diabetes, particularly type 1 and type 2 diabetes mellitus, and/or diabetic complications.

In addition compounds according to the invention are particularly suitable for the prevention or treatment of overweight, obesity (including class I, class II and/or class III obesity), visceral obesity and/or abdominal obesity.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include for example those which potentiate the therapeutic effect of an SGLT antagonist according to the invention with respect to one of the indications mentioned and/or which allow the dosage of an SGLT antagonist according to the invention to be reduced. Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK-431), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoid) receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully ⅕ of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the sodium-dependent glucose cotransporter SGLT. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of hydroxyl groups are not explicitly shown in every case in structural formulae. The Examples that follow are intended to illustrate the present invention without restricting it. The terms "room temperature" and "ambient temperature" are used interchangeably and denote temperatures of about 20° C. The following abbreviations are used:

tBu tert.butyl dba dibenzylidenaceton

DMF dimethylformamide

DMSO dimethyl sulfoxide

NMP N-methyl-2-pyrrolidone

THF tetrahydrofuran

Preparation of the Starting Compounds

Example I

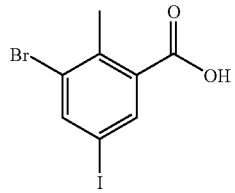

3-Bromo-5-iodo-2-methyl-benzoic Acid

N-Iodosuccinimide (5.8 g) is added in portions to an ice-cold solution of sulphuric acid (20 mL). The resulting mixture is stirred for 40 min before 2-bromo-3-methyl-benzoic acid (5.0 g) dissolved in sulphuric acid (20 mL) is added at such a rate that the solution temperature maintains below 5° C. The mixture is stirred at 5-10° C. for another 3 h before warming to room temperature overnight. Then, the mixture is poured on crushed ice (300 g) and the resultant solution is extracted with ethyl acetate. The combined extracts are washed in succession with aqueous 10% $Na_2S_2O_3$ solution (2×), water (3×), and brine (1×). After drying ($MgSO_4$) the organic layer, the solvent is evaporated under reduced pressure to give a solid. The solid is triturated with 70° C.-warm water, separated from the water by filtration and dried. After the solid is triturated with little ether, filtered and dried, the product is obtained as a white solid.

Yield: 4.9 g (62% of theory)

Mass spectrum (ESI$^-$): m/z=339/341 (Br) [M–H]$^-$

The following compounds may be obtained analogously to Example I:

(1) 4-Bromo-5-iodo-2-methyl-benzoic Acid

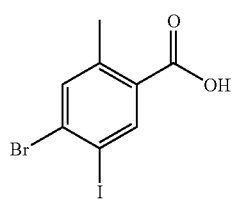

Mass spectrum (ESI$^-$): m/z=339/341 (Br) [M–H]$^-$ (2) 2-Bromo-5-iodo-3-methyl-benzoic Acid

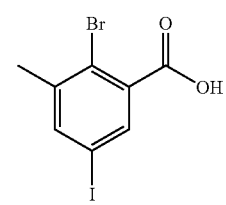

Mass spectrum (ESI$^-$): m/z=339/341 (Br) [M–H]$^-$ (3) 2-Bromo-5-iodo-4-methyl-benzoic Acid

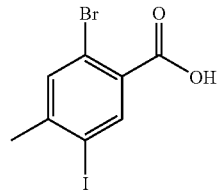

Mass spectrum (ESI$^-$): m/z=339/341 (Br) [M–H]$^-$ (4) (2-Bromo-5-iodo-4-methoxy-phenyl)-(4-ethyl-phenyl)-methanone

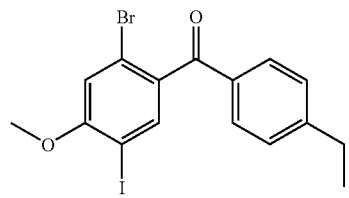

Mass spectrum (ESI$^+$): m/z=445/447 (Br) [M+H]$^+$

The starting material, (2-bromo-4-methoxy-phenyl)-(4-ethyl-phenyl)-methanone, is prepared as described under Examples II and III.

Example II

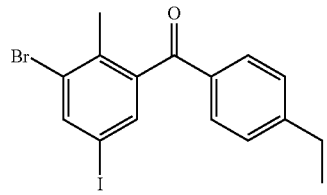

(3-Bromo-5-iodo-2-methyl-phenyl)-(4-ethyl-phenyl)-methanone

3-Bromo-5-iodo-2-methyl-benzoic acid (7.3 g) and $SOCl_2$ (70 mL) are combined in a flask connected with a reflux condenser. A few drops of DMF are added and the mixture is heated at reflux for 1 h. Then, the reaction solution is concentrated under reduced pressure and the residue is taken up in dichloromethane (80 mL) and ethylbenzene (15 mL). The resulting solution is cooled in an ice-bath and aluminum trichloride (7.2 g) is added in portions. Then, the cooling bath is removed and the reaction mixture is stirred at room temperature for 2 h. The reaction mixture is poured onto crushed ice and the organic phase is separated off. The aqueous phase is extracted with dichloromethane and the combined organic phases are washed in succession with 1 M hydrochloric acid, aqueous $NaHCO_3$ solution and brine. The organic phase is dried (sodium sulphate), the solvent is removed and the residue is chromatographed on silica gel (cyclohexane/ethyl acetate 20:1->9:1). The purified product is recrystallized from diisopropylether.

Yield: 2.6 g (28% of theory)

Mass spectrum (ESI$^+$): m/z=429/431 (Br) [M+H]$^+$

The following compounds may be obtained analogously to Example II:

(1) (4-Bromo-5-iodo-2-methyl-phenyl)-(4-ethyl-phenyl)-methanone

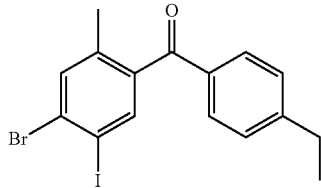

Mass spectrum (ESI⁺): m/z=429/431 (Br) [M+H]⁺

(2) (2-Bromo-5-iodo-3-methyl-phenyl)-(4-ethyl-phenyl)-methanone

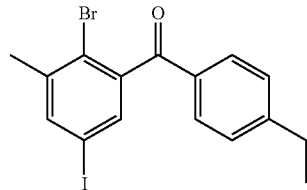

Mass spectrum (ESI⁺): m/z=429/431 (Br) [M+H]⁺

(3) (2-Bromo-5-iodo-4-methyl-phenyl)-(4-ethyl-phenyl)-methanone

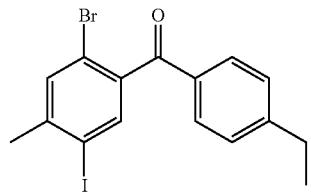

Mass spectrum (ESI⁺): m/z=429/431 (Br) [M+H]⁺

(4) (2-Bromo-4-fluoro-phenyl)-(4-ethyl-phenyl)-methanone

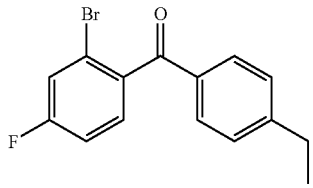

Mass spectrum (ESI⁺): m/z=307/309 (Br) [M+H]⁺

Example III

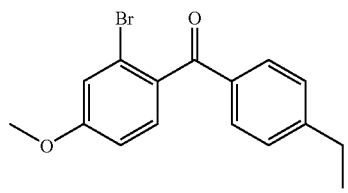

(2-Bromo-4-methoxy-phenyl)-(4-ethyl-phenyl)-methanone

Sodium methoxide (10.5 g) is added portionwise to (2-bromo-4-fluoro-phenyl)-(4-ethyl-phenyl)-methanone (43.0 g) dissolved in DMF (200 mL). The solution is stirred overnight, before another portion of sodium methoxide (5.5 g) is added. After another 3 h of stirring, water is added and the resulting mixture is extracted with ethyl acetate. The organic phase is dried (sodium sulphate), the solvent is removed and the residue is chromatographed on silica gel (cyclohexane/ethyl acetate 20:1->9:1).

Yield: 33.7 g (75% of theory)

Mass spectrum (ESI⁺): m/z=319/321 (Br) [M+H]⁺

Example IV

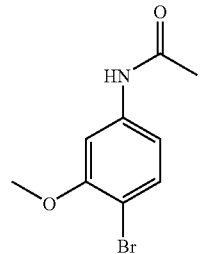

N-(4-Bromo-3-methoxy-phenyl)-acetamide

Acetic anhydride (13 mL) is added to an ice-cold solution of 4-bromo-3-methoxy-phenylamine (25.0 g) in acetic acid (100 mL). The mixture is stirred for 1 h and then diluted with ice-cold water (500 mL). The precipitate is separated by filtration, washed with water and dried at 60° C. to give the product.

Yield: 30.0 g (99% of theory)

Mass spectrum (ESI⁺): m/z=244/246 (Br) [M+H]⁺

Example V

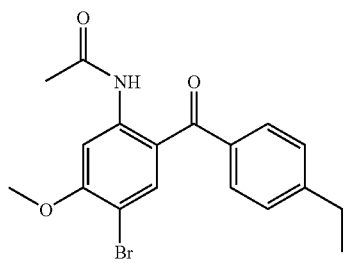

N-[4-Bromo-2-(4-ethyl-benzoyl)-5-methoxy-phenyl]-acetamide

Phosphorus oxychloride (17 mL) and tin(IV) chloride (5 mL) are successively added to a suspension of N-(4-bromo-3-methoxy-phenyl)-acetamide (5.0 g) and 4-ethylbenzoic acid (4.4 g) in 1,2-dichloroethane at such a rate that the temperature maintains below 35° C. The resulting mixture is heated at reflux temperature overnight. Then, the mixture is diluted with dichloromethane and poured onto crushed ice. After stirring the aqueous mixture for 30 min, the organic phase is separated and washed with 10% NaOH in water and water. The organic phase is dried (sodium sulphate), the solvent is removed and the residue is triturated with methanol to give the product.

Yield: 5.8 g (75% of theory)

Mass spectrum (ESI⁻): m/z=374/376 (Br) [M−H]⁻

Example VI

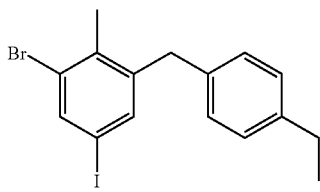

3-Bromo-5-(4-ethyl-benzyl)-1-iodo-4-methyl-benzene

A solution of (3-bromo-5-iodo-2-methyl-phenyl)-(4-ethyl-phenyl)-methanone (4.2 g) and triethylsilane (4.7 mL) in dichloromethane (10 mL) and acetonitrile (28 mL) is cooled in an ice-bath. Then, boron trifluoride diethyletherate (1.4 mL) is added dropwise over 3 min. The solution is stirred for 14 h at ambient temperature, before an aqueous 25% solution of KOH and diisopropylether are added. The organic phase is separated and the aqueous phase is extracted three times with diisopropylether. The combined organic phases are washed with 2 M potassium hydroxide solution and brine and then dried (sodium sulphate). After the solvent is evaporated, the residue is chromatographed on silica gel (cyclohexane/ethyl acetate 1:0->1:1).

Yield: 3.5 g (86% of theory)

The following compounds may be obtained analogously to Example VI:

(1) 2-Bromo-5-(4-ethyl-benzyl)-1-iodo-4-methyl-benzene

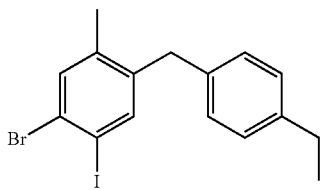

(2) 4-Bromo-3-(4-ethyl-benzyl)-1-iodo-5-methyl-benzene

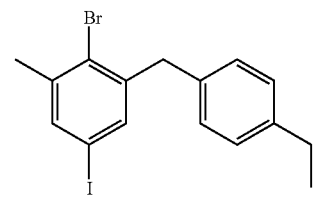

(3) 4-Bromo-5-(4-ethyl-benzyl)-1-iodo-2-methyl-benzene

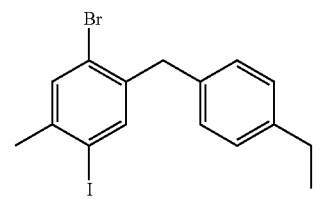

Mass spectrum (ESI$^+$): m/z=432/434 (Br) [M+NH$_4$]$^+$ (4) 4-Bromo-5-(4-ethyl-benzyl)-1-iodo-2-methoxy-benzene

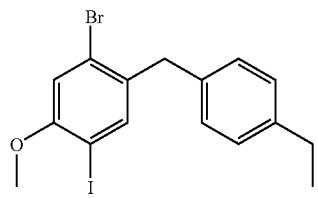

Mass spectrum (ESI$^+$): m/z=448/450 (Br) [M+NH$_4$]$^+$

Example VII

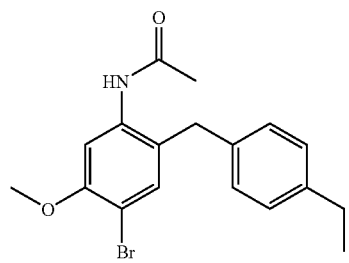

N-[4-Bromo-2-(4-ethyl-benzyl)-5-methoxy-phenyl]-acetamide

Sodium borohydride (0.17 g) is added portionwise to an ice-cold suspension of N-[4-bromo-2-(4-ethyl-benzoyl)-5-methoxy-phenyl]-acetamide (3.25 g) in ethanol (50 mL). The cooling bath is removed and the solution is stirred at ambient temperature for 2 h. Then, 1 M aqueous NaOH solution (8.5 mL) is added and the resulting solution is concentrated under reduced pressure. Water is added to the residue and the resulting mixture is extracted with ethyl acetate. The combined organic extracts are washed with brine, dried (Na$_2$SO$_4$) and concentrated. The residue is taken up in trifluoroacetic acid (20 mL) and triethylsilane (4.3 mL) is added. The solution is stirred at ambient temperature overnight and then poured on crushed ice. The resultant mixture is extracted twice with ethyl acetate. The combined extracts are washed with brine, dried (sodium sulphate) and concentrated under reduced pressure. The residue is treated with methanol and the precipitate formed is separated. The precipitate is then washed with diisopropylether and dried to give the desired product.

Yield: 2.8 g (89% of theory)

Mass spectrum (ESI$^+$): m/z=362/364 (Br) [M+H]$^+$

Example VIII

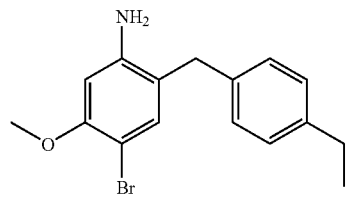

4-Bromo-2-(4-ethyl-benzyl)-5-methoxy-phenylamine

Half-concentrated hydrochloric acid (5 mL) is added to a solution of N-[4-bromo-2-(4-ethyl-benzyl)-5-methoxy-phenyl]-acetamide (2.8 g) in isopropanol (20 mL). The solution is heated at reflux temperature for 8 h and then concentrated under reduced pressure to remove most of the alcohol. Aqueous NaHCO$_3$ solution is added to the rest and the resulting mixture is extracted twice with ethyl acetate. The combined organic extracts are washed with brine, dried (Na$_2$SO$_4$) and concentrated to give the title compound.

Yield: 2.5 g (quantitative)

Mass spectrum (ESI$^+$): m/z=320/322 (Br) [M+H]$^+$

Example IX

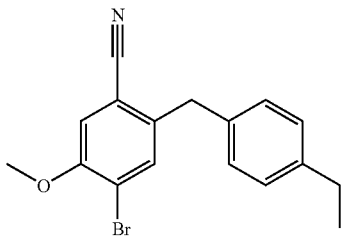

4-Bromo-2-(4-ethyl-benzyl)-5-methoxy-benzonitrile

Tert-butyl nitrite (1.1 mL) is added to a 60° C.-warm solution of CuCN (0.36 g) in DMSO (3 mL). Then, a solution of 4-bromo-2-(4-ethyl-benzyl)-5-methoxy-phenylamine (1.0 g) in DMSO is added dropwise and the resulting solution is stirred for 1 h at 60° C. After cooling to room temperature, the solution is acidified by the addition of 5 N aqueous hydrochloric acid. The resulting mixture is extracted with ethyl acetate and the combined extracts are dried (Na$_2$SO$_4$). After removal of the solvent, the residue is purified by chromatography on silica gel (cyclohexane/dichloromethane 3:1->1:3) to give the title compound.

Yield: 0.3 g (29% of theory)

Mass spectrum (ESI$^+$): m/z=347/349 (Br) [M+NH$_4$]$^+$

Example X

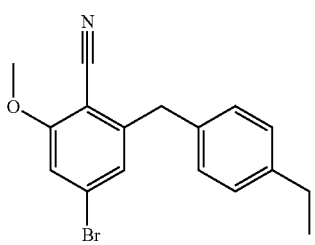

1-Bromo-4-cyano-3-methoxy-5-(4-ethyl-benzyl)-benzene

KOtBu (11.8 g) is added to a flask charged with a stir bar and dry NMP (40 mL) and chilled to –10° C. under argon atmosphere. A solution of ethyl (4-ethyl-phenyl)-acetate (10.1 g) and 1-bromo-4-cyano-3,5-difluoro-benzene (11.5 g) in NMP (40 mL) is added at such a rate that the reaction temperature maintains below 10° C. After stirring for 1 hour at room temperature, methanol (50 mL) and 1 M aqueous sodium hydroxide solution (39 mL) are added and the resulting mixture is stirred overnight at 100° C. Then, 4 M aqueous hydrochloric acid (100 mL) is added and the mixture is stirred for another h at 100° C. The methanol fraction is evaporated, water (200 mL) is added to the residue and the resulting mixture is extracted with ethyl acetate. The combined organic extracts are washed twice with water, twice with brine and dried (MgSO$_4$). The solvent is evaporated and the residue is washed with methanol. The insoluble residue is separated by filtration and dried to give the white product.

Yield: 10.0 g (58% of theory)

Mass spectrum (ESI$^+$): m/z=330/332 (Br) [M+H]$^+$

Example XI

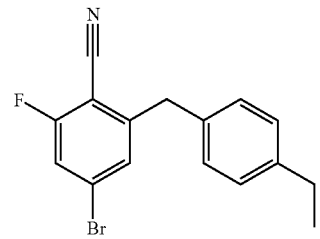

1-Bromo-4-cyano-3-fluoro-5-(4-ethyl-benzyl)-benzene

KOtBu (6.7 g) is added to a flask charged with a stir bar and dry NMP (30 mL) and chilled to –10° C. under argon atmosphere. A solution of ethyl (4-ethyl-phenyl)-acetate (5.6 g) and 1-bromo-4-cyano-3,5-difluoro-benzene (6.4 g) in NMP (20 mL) is added at such a rate that the solution temperature maintains below 10° C. After stirring for 1 hour at 10° C., the solution is neutralized with 1 M aqueous hydrochloric acid and extracted with ethyl acetate. The combined extracts are dried (Na$_2$SO$_4$) and the solvent is evaporated. The residue is dissolved in THF (20 mL) and treated with 1M aqueous NaOH solution (80 mL). After stirring overnight at room temperature, the solution is acidified with 4 M HCl solution and extracted with ethyl acetate. The organic extracts are combined and dried (Na$_2$SO$_4$) and the solvent is evaporated. The residue is dissolved in DMF (25 mL) and K$_2$CO$_3$ (5.5 g) is added. The resulting mixture is stirred at 100° C. for 1 h. After cooling to room temperature, the mixture is neutralized with 1 M aqueous hydrochloric acid and the resultant mixture is extracted with ethyl acetate. The combined organic extracts are dried (MgSO$_4$) and the solvent is evaporated. The residue is purified by chromatography on silica gel (cyclohexane/ethyl acetate 1:0->1:1).

Yield: 4.8 g (51% of theory)

Mass spectrum (ESI$^+$): m/z=317/319 (Br) [M]$^+$

Example XII

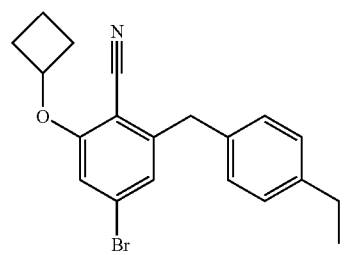

1-Bromo-4-cyano-3-cyclobutoxy-5-(4-ethyl-phenyl)-benzene

1-Bromo-4-cyano-3-fluoro-5-(4-ethyl-phenyl)-benzene (1.2 g) is added to a flask charged with a stir bar, KOtBu (0.5 g) and cyclobutanol (3.0 g). The solution is stirred at room temperature overnight, before another portion of KOtBu (0.2 g) is added. The solution is stirred for another 5 h and then neutralized with 1 M aqueous HCl solution. The resulting mixture is extracted with ethyl acetate, the combined organic phases are dried (sodium sulphate) and the solvent is removed to give the title compound.

Yield: 1.28 g (92% of theory)

The following compounds may be obtained analogously to Example XII:

(1) 1-Bromo-4-cyano-5-(4-ethyl-benzyl)-3-isopropoxy-benzene

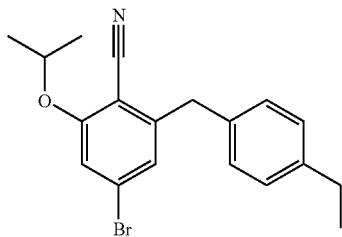

The compound is prepared using isopropanol instead of cyclobutanol according to the procedure described above.

(2) 1-Bromo-4-cyano-3-ethoxy-5-(4-ethyl-benzyl)-benzene

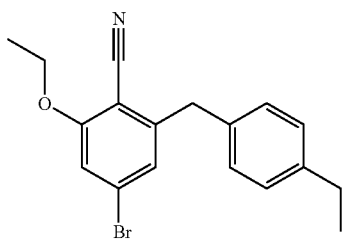

The compound is prepared using ethanol instead of cyclobutanol according to the procedure described above.

(3) 1-Bromo-4-cyano-5-(4-ethyl-benzyl)-3-methylsulfanyl-benzene

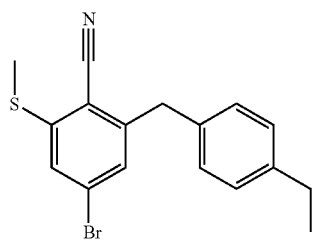

The compound is prepared using sodium methylsulfide in dimethylformamide at 100° C. Mass spectrum (ESI$^+$): m/z=346/348 (Br) [M+H]$^+$ Example XIII

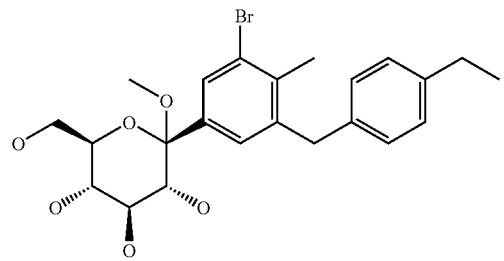

1-Bromo-3-(4-ethylbenzyl)-5-(1-methoxy-D-glucopyranos-1-yl)-2-methyl-benzene

A solution of iPrMgCl*LiCl in THF (1 mol/L, 10 mL) is added dropwise to a −60° C.-cold solution of 3-bromo-5-(4-ethyl-benzyl)-1-iodo-4-methyl-benzene (3.5 g) in THF (20 mL). The solution is warmed to −20° C. over a period of 1 h and then a solution of 2,3,4,6-tetrakis-β-(trimethylsilyl)-D-glucopyranone (4.8 g) in tetrahydrofuran (3 mL) is added to the solution. The resulting solution is slowly warmed to −5° C. and stirred for 6 h. The reaction is quenched with aqueous NH$_4$Cl solution and the resulting mixture is extracted with ethyl acetate. The combined organic extracts are washed with brine and dried (sodium sulphate). After the removal of the solvent, the residue is dissolved in methanol (30 mL) and treated with methanesulfonic acid (0.3 mL). The solution is stirred at 40° C. for 6 h and then neutralized by the addition of solid NaHCO$_3$. The solvent is removed under reduced pressure and the residue is taken up in ethyl acetate. The organic solution is washed with water and brine and dried (sodium sulphate). After the removal of the solvent, the crude product is submitted to reduction without further purification.

Yield: 4.2 g (crude product)

The following compounds may be obtained analogously to Example XIII:

(1) 1-Bromo-4-(4-ethylbenzyl)-2-(1-methoxy-D-glucopyranos-1-yl)-5-methyl-benzene

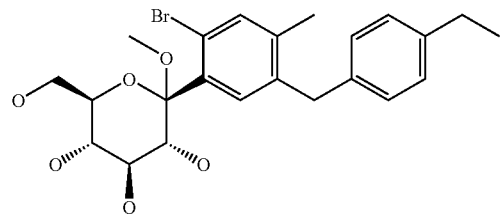

(2) 1-Bromo-2-(4-ethylbenzyl)-4-(1-methoxy-D-glucopyranos-1-yl)-6-methyl-benzene

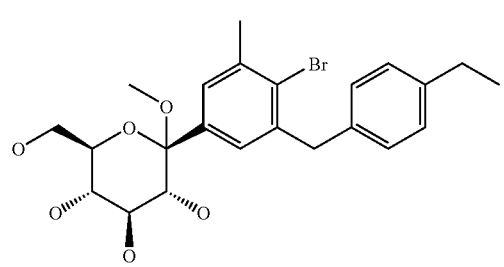

(3) 1-Bromo-2-(4-ethylbenzyl)-4-(1-methoxy-D-glucopyranos-1-yl)-5-methoxy-benzene

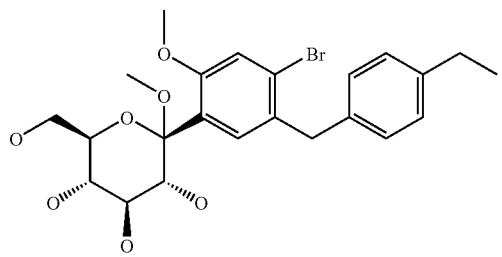

(4) 2-(4-ethylbenzyl)-4-(1-methoxy-D-glucopyranos-1-yl)-5-methoxy-benzonitrile

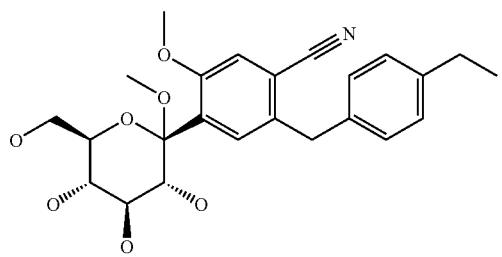

4-Bromo-2-(4-ethyl-benzyl)-5-methoxy-benzonitrile is used as starting material. 2-(4-Ethyl-benzyl)-4-iodo-5-methoxy-benzonitrile may be used as starting material as well.

Example XIV

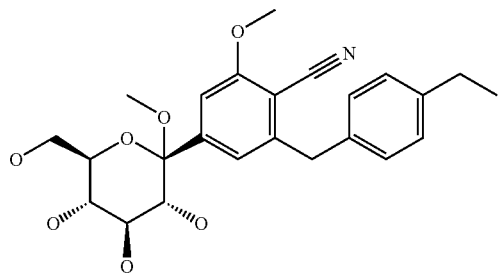

6-(4-Ethylbenzyl)-2-methoxy-4-(1-methoxy-D-glucopyranos-1-yl)-benzonitrile

A 1.7 M solution of tBuLi in pentane (18.3 mL) cooled to −78° C. is added dropwise to a solution of 1-bromo-4-cyano-5-(4-ethyl-benzyl)-3-methoxy-benzene (5.0 g) in hexane (40 mL) and THF (20 mL) chilled to −78° C. nBuLi or sBuLi instead of tBuLi may be used as well. After complete addition and 15 min of stirring, a solution of 2,3,4,6-tetrakis-O-(trimethylsilyl)-D-glucopyranone (90%, 7.9 g) in hexane (30 mL) cooled to −78° is added via a transfer needle. The resulting solution is stirred at −70° C. for 2 h and then slowly warmed to −5° C. The reaction is quenched with 1% acetic acid in water (100 mL) and the resulting mixture is extracted with ethyl acetate. The combined organic extracts are washed with brine and dried (sodium sulphate). After the removal of the solvent, the residue is dissolved in methanol (50 mL) and treated with methanesulfonic acid (2.5 mL) to produce the desired more stable anomeric linkage. The solution is stirred at 50° C. overnight and then neutralized by the addition of solid NaHCO$_3$. The solvent is removed under reduced pressure and the residue is taken up in ethyl acetate. The organic solution is washed with water and brine and dried (sodium sulphate). After the removal of the solvent, the crude product is purified by chromatography on silica gel (dichloromethane/methanol 1:0->2:1).

Yield: 0.5 g (7% of theory)

The following compounds may be obtained analogously to Example XIV:

(1) 2-Cyclobutoxy-6-(4-ethylbenzyl)-4-(1-methoxy-D-glucopyranos-1-yl)-benzonitrile

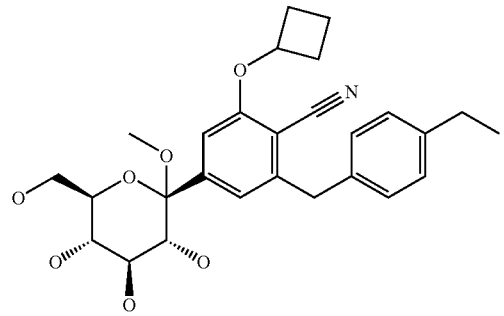

(2) 6-(4-Ethylbenzyl)-2-isopropoxy-4-(1-methoxy-D-glucopyranos-1-yl)-benzonitrile

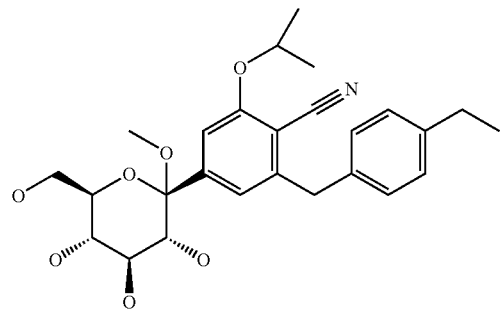

(3) 2-Ethoxy-6-(4-ethylbenzyl)-4-(1-methoxy-D-glucopyranos-1-yl)-benzonitrile

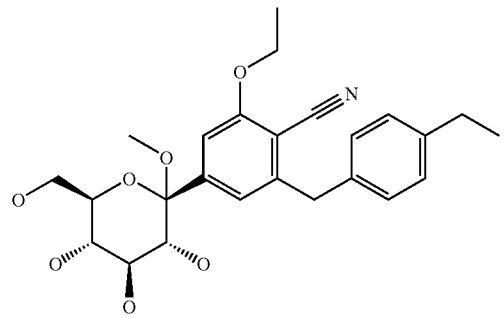

(4) 6-(4-Ethylbenzyl)-4-(1-methoxy-D-glucopyranos-1-yl)-6-methylsulfanyl-benzonitrile

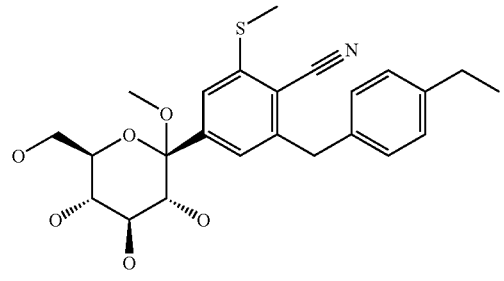

(5) 2-(4-Ethylbenzyl)-4-(1-methoxy-D-glucopyranos-1-yl)-5-methoxy-benzonitrile

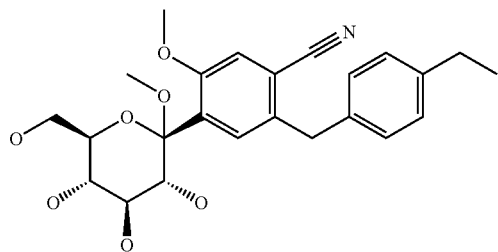

Example XV

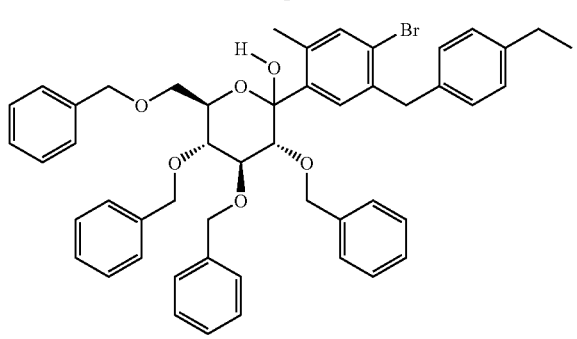

1-Bromo-2-(4-ethylbenzyl)-4-(1-hydroxy-2,3,4,6-tetra-O-benzyl-D-glucopyranos-1-yl)-5-methyl-benzene A 1.6 M solution of nBuLi in hexane (10.5 mL) is added dropwise to a solution of 4-bromo-5-(4-ethyl-benzyl)-1-iodo-2-methyl-benzene (7.0 g) in THF (70 mL) chilled to −78° C. After stirring the resulting solution at −78° C. for 1 h, a solution of 2,3,4,6-tetrakis-O-benzyl-D-glucopyranone (9.1 g) in tetrahydrofuran (30 mL) pre-cooled to −70° C. is added via transfer needle. The resulting solution is stirred at −75° C. for 3 h, before the reaction is quenched by the addition of aqueous NH$_4$Cl solution. The resulting mixture is extracted with ethyl acetate, the combined extracts are washed with brine and dried (magnesium sulphate). After the removal of the solvent, the residue is purified by chromatography on silica gel (cyclohexane/ethyl acetate 4:1->1:1).

Yield: 7.5 g (54% of theory)

Mass spectrum (ESI$^+$): m/z=844/846 (Br) [M+NH$_4$]$^+$

The following compound may be obtained analogously to Example XV:

(1) 2-(4-Ethylbenzyl)-4-(1-hydroxy-2,3,4,6-tetra-O-benzyl-D-glucopyranos-1-yl)-5-methoxy-benzonitrile

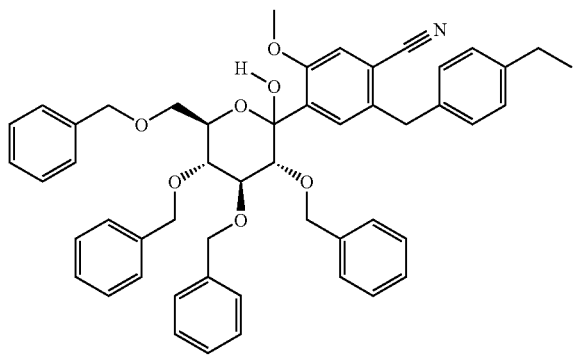

4-Bromo-2-(4-ethyl-benzyl)-5-methoxy-benzonitrile is used as starting material. The generation of the organometallic aglycon may also be performed using tertBuLi instead of nBuLi delivering the lithiated aglycon or employing iPrMgCl*LiCl, iPr$_2$Mg*LiCl or nBu$_3$MgLi giving the magnesiated derivative; all these organometal species add to the gluconolactone to deliver the desired intermediate. 2-(4-Ethyl-benzyl)-4-iodo-5-methoxy-benzonitrile may be used as starting material as well.

Example XVI

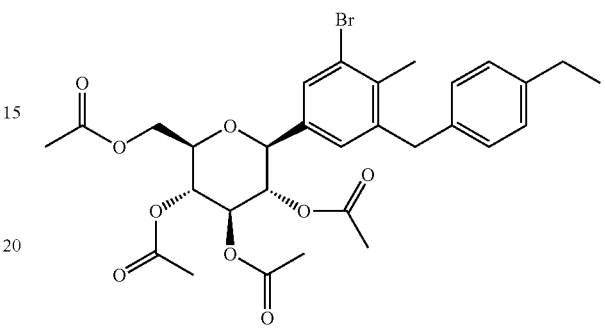

1-Bromo-3-(4-ethylbenzyl)-2-methyl-5-(2,3,4,6-tetra-O-acetyl-β-D-glucopyranos-1-yl)-benzene A solution of 1-bromo-3-(4-ethylbenzyl)-5-(1-methoxy-D-glucopyranos-1-yl)-2-methyl-benzene (4.2 g) and triethylsilane (3.5 mL) in dichloromethane (30 mL) and acetonitrile (90 mL) is cooled to −15° C. Then boron trifluoride diethyletherate (2.1 mL) is added dropwise at such a rate that the solution temperature maintains below −5° C. The resultant solution is stirred in an ice-bath for another 0.5 h and then the reaction is quenched by the addition of aqueous sodium hydrogen carbonate solution. The resulting mixture is stirred at room temperature for 0.5 h and then the organic layer is separated and the aqueous layer is extracted with ethyl acetate. The combined organic layers are washed with brine and dried (sodium sulphate). The solvent is removed and the residue is taken up in dichloromethane (50 mL). The resultant solution is cooled in an ice-bath and pyridine (4.0 mL), acetic anhydride (4.3 mL) and 4-dimethylaminopyridine (0.1 g) are added in succession. The solution is stirred at ambient temperature for 1 h and then diluted with dichloromethane (100 mL). The organic solution is washed twice with hydrochloric acid (1 mol/l in water) and dried (sodium sulphate). After evaporation of the solvent under reduced pressure, the residue is recrystallized from ethanol.

Yield: 2.7 g (53% of theory)

Mass spectrum (ESI$^+$): m/z=636/638 (Br) [M+NH$_4$]$^+$

The following compounds may be obtained analogously to Example XVI:

(1) 1-Bromo-4-(4-ethylbenzyl)-2-(2,3,4,6-tetra-O-acetyl-β-D-glucopyranos-1-yl)-5-methyl-benzene

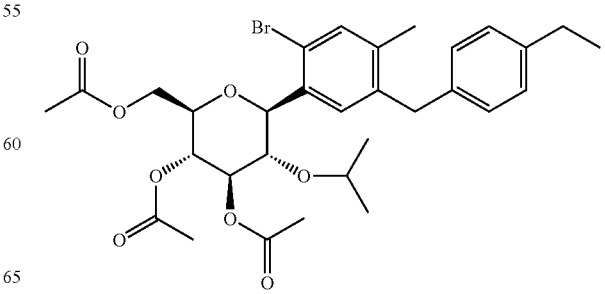

Mass spectrum (ESI$^+$): m/z=636/638 (Br) [M+NH$_4$]$^+$ (2) 1-Bromo-2-(4-ethylbenzyl)-4-(2,3,4,6-tetra-O-acetyl-β-D-glucopyranos-1-yl)-6-methyl-benzene

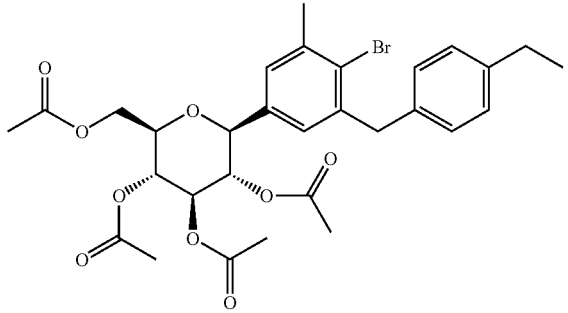

Mass spectrum (ESI⁺): m/z=636/638 (Br) [M+NH₄]⁺

(3) 1-Bromo-2-(4-ethylbenzyl)-4-(2,3,4,6-tetra-O-acetyl-β-D-glucopyranos-1-yl)-5-methoxy-benzene

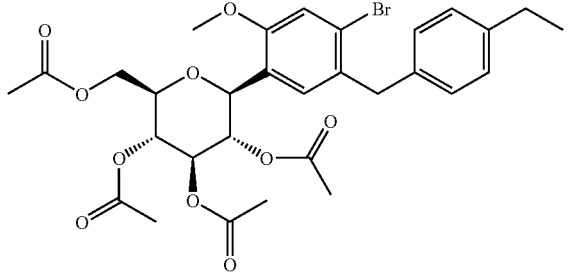

Mass spectrum (ESI⁺): m/z=652/654 (Br) [M+NH₄]⁺

(4) 6-(4-Ethylbenzyl)-4-(2,3,4,6-tetra-O-acetyl-β-D-glucopyranos-1-yl)-2-methoxy-benzonitrile

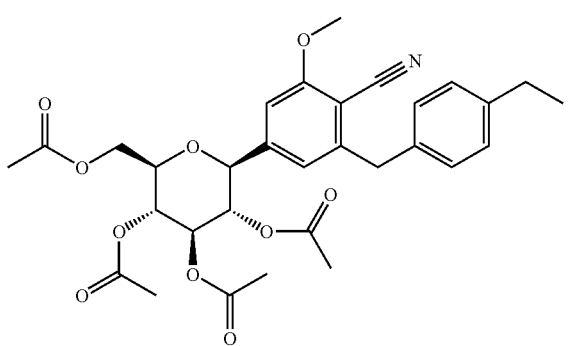

The reduction is conducted on 6-(4-ethylbenzyl)-4-(1-methoxy-D-glucopyranos-1-yl)-2-methoxy-benzonitrile using the procedure described above.

(5) 2-Cyclobutoxy-6-(4-ethylbenzyl)-4-(2,3,4,6-tetra-O-acetyl-β-D-glucopyranos-1-yl)-benzonitrile

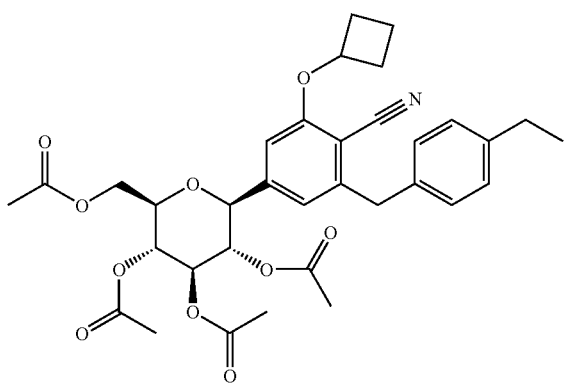

The reduction is conducted on 2-cyclobutoxy-6-(4-ethylbenzyl)-4-(1-methoxy-D-glucopyranos-1-yl)-benzonitrile using the procedure described above.

(6) 2-(4-Ethylbenzyl)-4-(2,3,4,6-tetra-O-acetyl-δ-D-glucopyranos-1-yl)-5-methoxy-benzonitrile

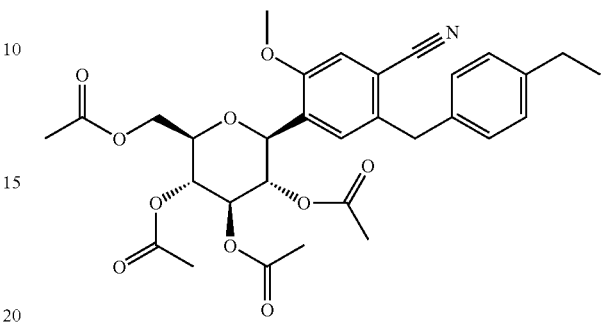

The reduction is conducted on 2-(4-ethylbenzyl)-4-(1-methoxy-D-glucopyranos-1-yl)-5-methoxy-benzonitrile using the procedure described above.

Mass spectrum (ESI⁺): m/z=599 [M+NH₄]⁺

Example XVII

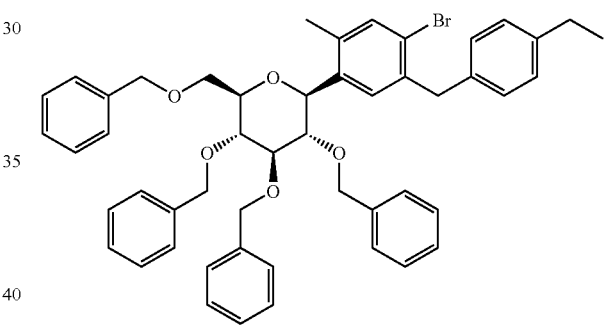

1-Bromo-2-(4-ethylbenzyl)-5-methyl-5-(2,3,4,6-tetra-O-benzyl-β-D-glucopyranos-1-yl)-benzene A solution of 1-bromo-2-(4-ethylbenzyl)-4-(1-hydroxy-D-glucopyranos-1-yl)-5-methyl-benzene (7.5 g) and triethylsilane (7.3 mL) in dichloromethane (100 mL) is cooled to −40° C. under argon atmosphere. Then, boron trifluoride diethyletherate (3.4 mL) is added dropwise at such a rate that the solution temperature maintains below −30° C. The resultant solution is stirred at −20° C. for another 2 h and then the reaction is quenched by the addition of aqueous sodium hydrogen carbonate solution. The organic layer is separated and the aqueous layer is extracted with dichloromethane. The combined organic layers are washed with brine and dried (magnesium sulphate). The solvent is removed and the residue is treated with 50° C.-warm ethanol for 10 min. The insoluble remainder is separated by filtration and washed twice with ethanol. After drying the title compound is yielded.

Yield: 4.2 g (57% of theory)

Mass spectrum (ESI⁺): m/z=828/830 (Br) [M+NH₄]⁺

The following compound may be obtained analogously to Example XVII:

(1) 2-(4-Ethylbenzyl)-4-(2,3,4,6-tetra-O-benzyl-β-D-glucopyranos-1-yl)-5-methoxy-benzonitrile

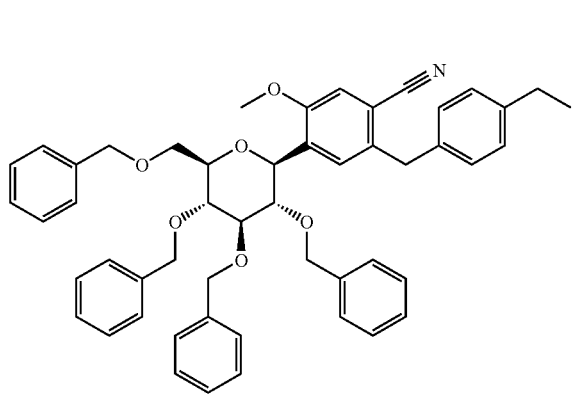

The reduction is conducted on 2-(4-ethylbenzyl)-4-(1-hydroxy-2,3,4,6-tetra-O-benzyl-D-glucopyranos-1-yl)-5-methoxy-benzonitrile using the procedure described above.

Example XVIII

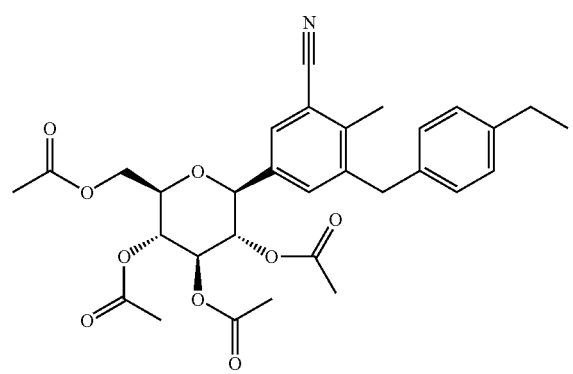

1-Cyano-3-(4-ethylbenzyl)-2-methyl-5-(2,3,4,6-tetra-O-acetyl-β-D-glucopyranos-1-yl)-benzene A flask is charged with a stir bar, 1-bromo-3-(4-ethylbenzyl)-2-methyl-5-(2,3,4,6-tetra-β-acetyl-β-D-glucopyranos-1-yl)-benzene (1.0 g), zinc (5 mg), zinc cyanide (0.21 g), Pd$_2$(dba)$_3$*CHCl$_3$ (34 g) and tri-tertbutylphosphonium tetrafluoroborate (19 mg) and put under Ar atmosphere. Degassed NMP (2 mL) is added and the mixture is stirred at room temperature for 16 h (Alternatively, the starting glucoside dissolved in NMP is added). Then, ethyl acetate is added, the resulting mixture is filtered and the filtrate is washed with aqueous NaHCO$_3$ solution. After drying (sodium sulphate) of the organic solution, the solvent is removed under reduced pressure and the residue is recrystallized from ethanol to yield the purified product.

Yield: 0.9 g (99% of theory)

Mass spectrum (ESI$^+$): m/z=583 [M+NH$_4$]$^+$

The following compounds may be obtained analogously to Example XVIII:

(1) 1-Cyano-4-(4-ethylbenzyl)-2-(2,3,4,6-tetra-O-acetyl-β-D-glucopyranos-1-yl)-5-methyl-benzene

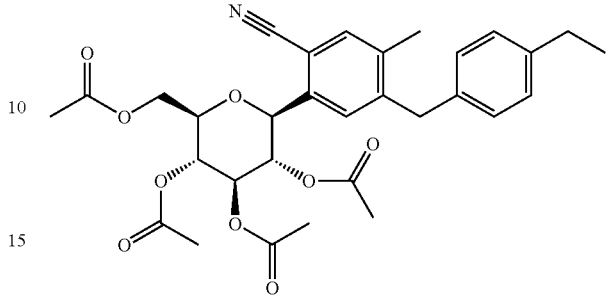

(2) 1-Cyano-2-(4-ethylbenzyl)-4-(2,3,4,6-tetra-O-acetyl-β-D-glucopyranos-1-yl)-5-methyl-benzene

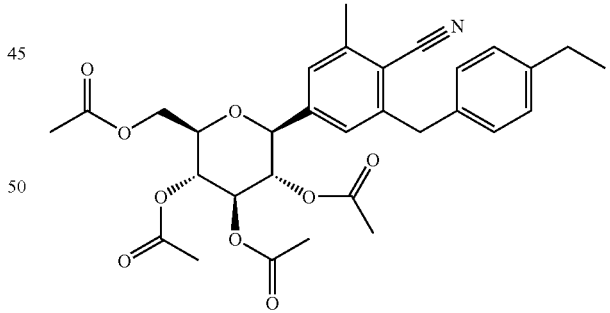

Example XIX

1-Cyano-2-(4-ethylbenzyl)-4-(2,3,4,6-tetra-O-acetyl-β-D-glucopyranos-1-yl)-6-methyl-benzene A microwave oven suited vessel is charged with 1-bromo-2-(4-ethylbenzyl)-6-methyl-4-(2,3,4,6-tetra-O-acetyl-β-D-glucopyranos-1-yl)-benzene (0.2 g), nickel(II) cyanide tetrahydrate (40 mg) and NMP (0.5 mL). This mixture is heated with stirring in a microwave oven at 200° C. for 90 min. Then, ethyl acetate is added, the resulting mixture is filtered and the filtrate is concentrated to give the crude product that is submitted to global deprotection without further purification.

Example XX

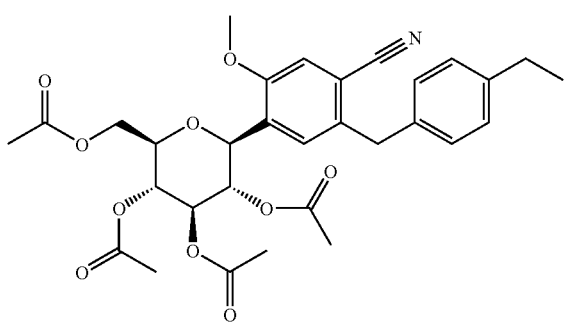

2-(4-Ethylbenzyl)-5-methoxy-4-(2,3,4,6-tetra-O-acetyl-(β-D-glucopyranos-1-yl)-benzonitrile A flask charged with a stir bar, 1-bromo-2-(4-ethylbenzyl)-5-methoxy-4-(2,3,4,6-tetra-O-acetyl-β-D-glucopyranos-1-yl)-benzene (1.6 g), copper(I) cyanide (0.56 g) and NMP (10 mL) is stirred at 215° C. for 3 h. Then, water is added and the precipitate is separated by filtration. The precipitate is dissolved in ethyl acetate (50 mL) and filtered over Celite. The filtrate is dried ($Na_2SO_4$) and concentrated. The residue is purified by chromatography on silica gel (cyclohexane/ethyl acetate 2:1->1:2).

Yield: 1.1 g (75% of theory)

Mass spectrum ($ESI^+$): m/z=583 $[M+NH_4]^+$

This compound can also be prepared using the procedures described for Examples XVI, XVIII and XIX.

Example XXI

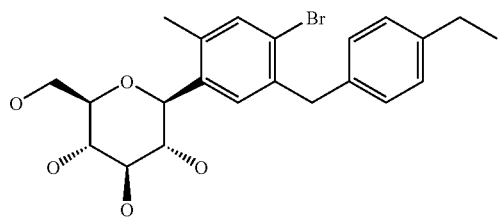

1-Bromo-2-(4-ethylbenzyl)-4-(β-D-glucopyranos-1-yl)-5-methyl-benzene

At ambient temperature a 1 M solution of $BCl_3$ in $CH_2Cl_2$ (6.2 mL) is added dropwise to a solution of 1-bromo-2-(4-ethylbenzyl)-5-methyl-4-(2,3,4,6-tetra-O-benzyl-β-D-glucopyranos-1-yl)-benzene (1.0 g) and pentamethylbenzene (2.4 g) in $CH_2Cl_2$ (25 mL). After complete addition, the solution is stirred at room temperature for 2 h. Then, methanol (5 mL) is added and the resulting solution is stirred for another 10 min. The solution is concentrated under reduced pressure and the residue is purified by chromatography on silica gel (dichloromethane/methanol 10:1->3:1).

Yield: 0.49 g (88% of theory)

Mass spectrum ($ESI^+$): m/z=468/470 $[M+NH_4]^+$

The following compound may be obtained analogously to Example XXI:

(1) 2-(4-Ethylbenzyl)-4-β-D-glucopyranos-1-yl)-5-methoxy-benzonitrile

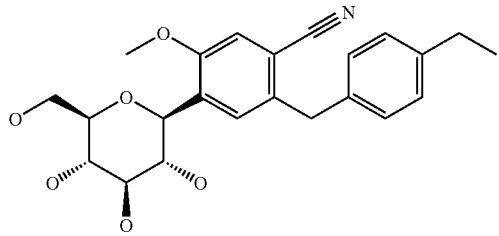

Mass spectrum ($ESI^+$): m/z=431 $[M+NH_4]^+$

Preparation of the End Compounds

Example 1

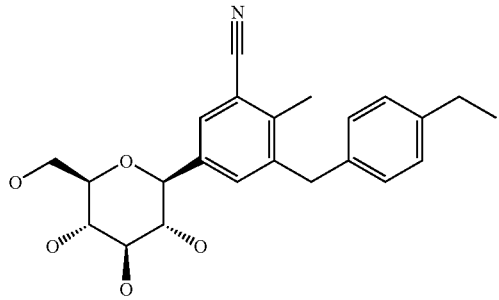

1-Cyano-3-(4-ethylbenzyl)-5-(β-D-glucopyranos-1-yl)-2-methyl-benzene

Aqueous sodium hydroxide solution (1.7 mL, 4 mol/L) is added to 1-cyano-3-(4-ethylbenzyl)-2-methyl-5-(2,3,4,6-tetra-O-acetyl-β-D-glucopyranos-1-yl)-benzene (0.85 g) dissolved in methanol (6 mL) and THF (3 mL). The solution is stirred at room temperature for 1 h and then neutralized with hydrochloric acid (1 mol/L). After removal of the organic solvents, the residue is diluted with aqueous sodium bicarbonate solution and the resulting mixture is extracted with ethyl acetate. The combined organic extracts are dried (sodium sulphate) and the solvent is evaporated. The remainder is purified by chromatography on silica gel (dichloromethane/methanol 1:0->8:1).

Yield: 0.45 g (75% of theory)

Mass spectrum ($ESI^+$): m/z=415 $[M+NH_4]^+$

The following compounds may be obtained analogously to Example 1:

(2) 1-Cyano-4-(4-ethylbenzyl)-2-(β-D-glucopyranos-1-yl)-5-methyl-benzene

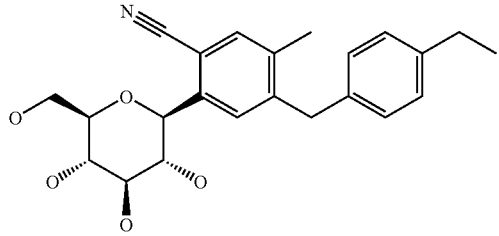

(3) 1-Cyano-2-(4-ethylbenzyl)-4-(β-D-glucopyranos-1-yl)-6-methyl-benzene

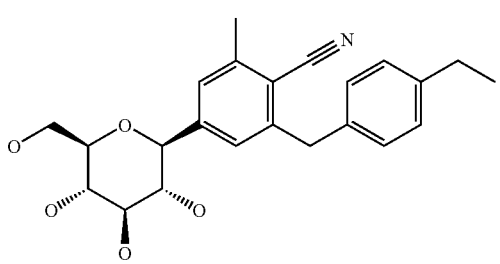

Mass spectrum (ESI⁺): m/z=415 [M+NH$_4$]$^+$

(4) 2-(4-Ethylbenzyl)-4-(β-D-glucopyranos-1-yl)-5-methoxy-benzonitrile

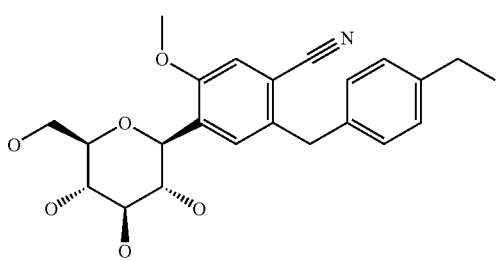

Mass spectrum (ESI⁺): m/z=431 [M+NH$_4$]$^+$
This compound may also be obtained as described under Example XXI.

(5) 6-(4-Ethylbenzyl)-4-(β-D-glucopyranos-1-yl)-2-methoxy-benzonitrile

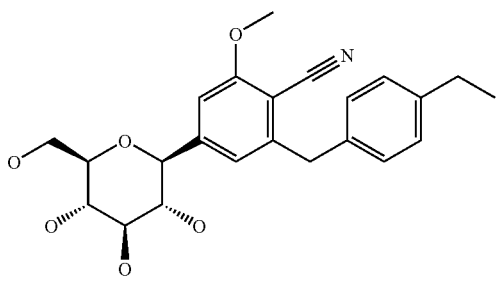

Mass spectrum (ESI⁺): m/z=431 [M+NH$_4$]$^+$

(6) 2-Cyclobutoxy-6-(4-ethylbenzyl)-4-(β-D-glucopyranos-1-yl)-benzonitrile

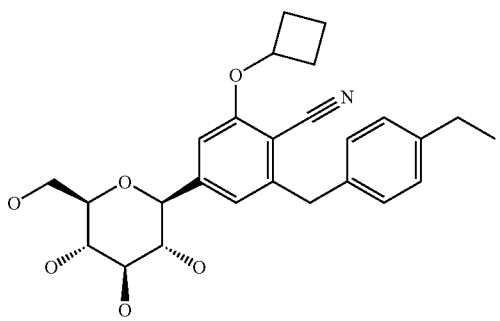

Mass spectrum (ESI⁻): m/z=498 [M+HCOO]$^-$

Example 7

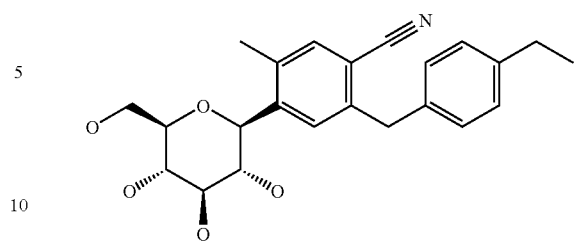

1-Cyano-2-(4-ethylbenzyl)-4-(β-D-glucopyranos-1-yl)-5-methyl-benzene

A microwave oven-suited vessel charged with a stir bar, 1-bromo-2-(4-ethylbenzyl)-4-(β-D-glucopyranos-1-yl)-5-methyl-benzene (0.40 g), Ni(CN)$_2$ and NMP (4 mL) and flushed with argon is heated in a microwave oven at 220° C. for 1 h. Then, water is added and the resulting mixture is extracted with ethyl acetate. The combined organic extracts are dried (sodium sulphate) and the solvent is evaporated. The remainder is purified by chromatography on silica gel (dichloromethane/methanol 1:0->8:1).

Yield: 0.30 g (85% of theory)
Mass spectrum (ESI⁺): m/z=415 [M+NH$_4$]$^+$

Example 8

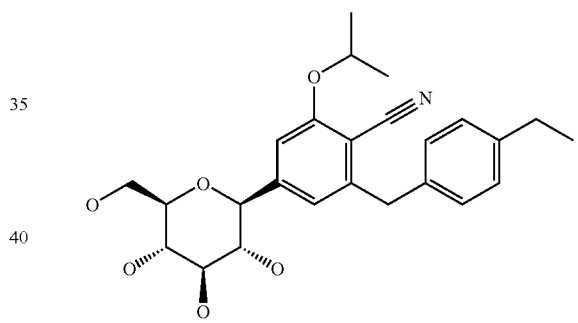

6-(4-Ethylbenzyl)-4-(β-D-glucopyranos-1-yl)-2-isopropoxy-benzonitrile

A solution of 1-cyano-6-(4-ethylbenzyl)-2-isopropoxy-4-(1-methoxy-D-glucopyranos-1-yl)-benzene (1.0 g) and triethylsilane (1.0 mL) in dichloromethane (6 mL) and acetonitrile (8 mL) is cooled to −20° C. Then boron trifluoride diethyletherate (0.7 mL) is added dropwise at such a rate that the solution temperature maintains below −10° C. The resultant solution is warmed to 5° C. over a period of 2 h and then the reaction is quenched by the addition of aqueous sodium hydrogen carbonate solution. The organic solvent is removed under reduced pressure and the residue is extracted with ethyl acetate. The combined organic extracts are dried (sodium sulphate) and the solvent is removed. The residue is purified by HPLC on reverse phase (YMC C18, acetonitrile/water) to give the pure product.

Yield: 0.1 g (10% of theory)
Mass spectrum (ESI⁺): m/z=459 [M+NH$_4$]$^+$

The following compounds may be obtained analogously to Example 8:

(9) 2-Ethoxy-6-(4-ethylbenzyl)-4-(β-D-glucopyranos-1-yl)-benzonitrile

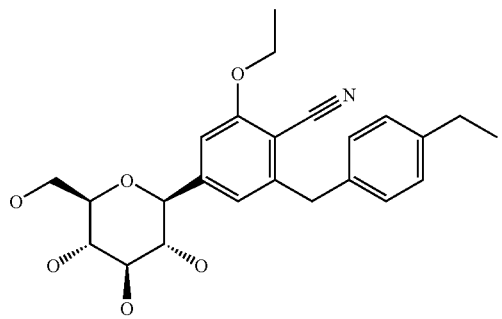

Mass spectrum (ESI+): m/z=445 [M+NH4]+

(10) 6-(4-Ethylbenzyl)-4-(β-D-glucopyranos-1-yl)-2-methylsulfanyl-benzonitrile

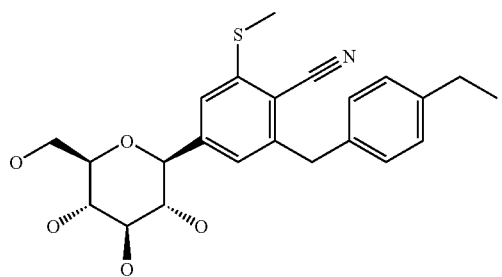

Mass spectrum (ESI+): m/z=447 [M+NH4]+

Example 11

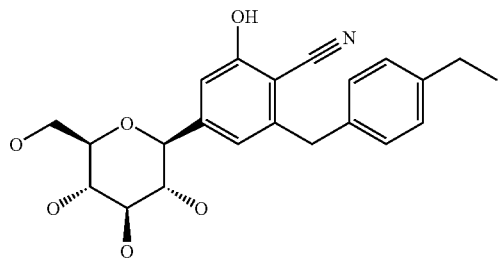

6-(4-Ethylbenzyl)-4-(β-D-glucopyranos-1-yl)-2-hydroxy-benzonitrile

A mixture of 6-(4-ethylbenzyl)-2-methoxy-4-(2,3,4,6-tetra-O-acetyl-β-D-glucopyranos-1-yl)-benzonitrile (0.36 g) and pyridinium hydrochloride (0.72 g) is heated at 215° C. for 1.5 h. After cooling to ambient temperature, the mixture is dissolved in methanol (8 mL) and treated with 4 M aqueous NaOH solution (2.5 mL). The solution is stirred at room temperature for 1 h and then acidified using hydrochloric acid (4 mol/L). After removal of the organic solvents, the residue is extracted with ethyl acetate, the combined organic extracts are dried (sodium sulphate) and the solvent is evaporated. The remainder is purified by HPLC on reversed phase (YMC C18, acetonitrile/water).

Yield: 0.13 g (50% of theory)

Mass spectrum (ESI+): m/z=417 [M+NH4]+

The following compound may be obtained analogously to Example 11:

(12) 2-(4-Ethylbenzyl)-4-(β-D-glucopyranos-1-yl)-5-hydroxy-benzonitrile

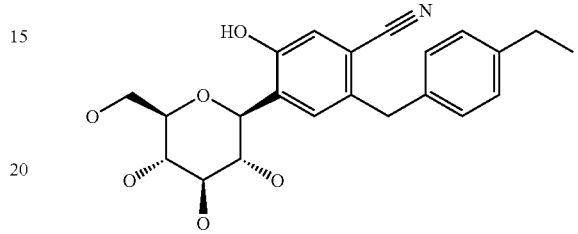

Mass spectrum (ESI+): m/z=417 [M+NH4]+

The following compounds are also prepared analogously to the above-mentioned Examples and other methods known from the literature:

| Ex. | Structure |
|---|---|
| 13 | 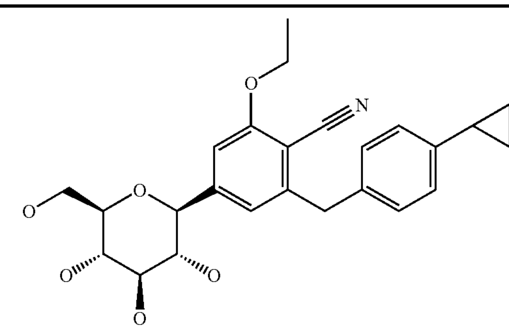 |
| 14 | 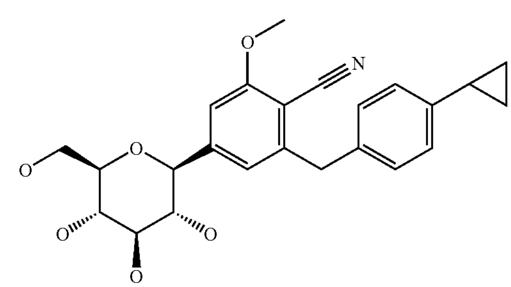 |
| 15 | 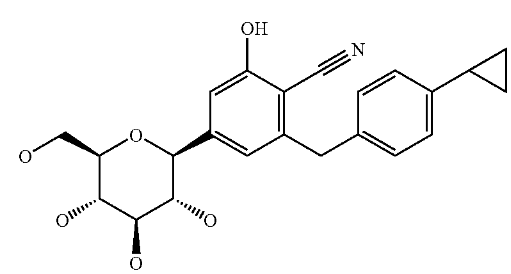 |

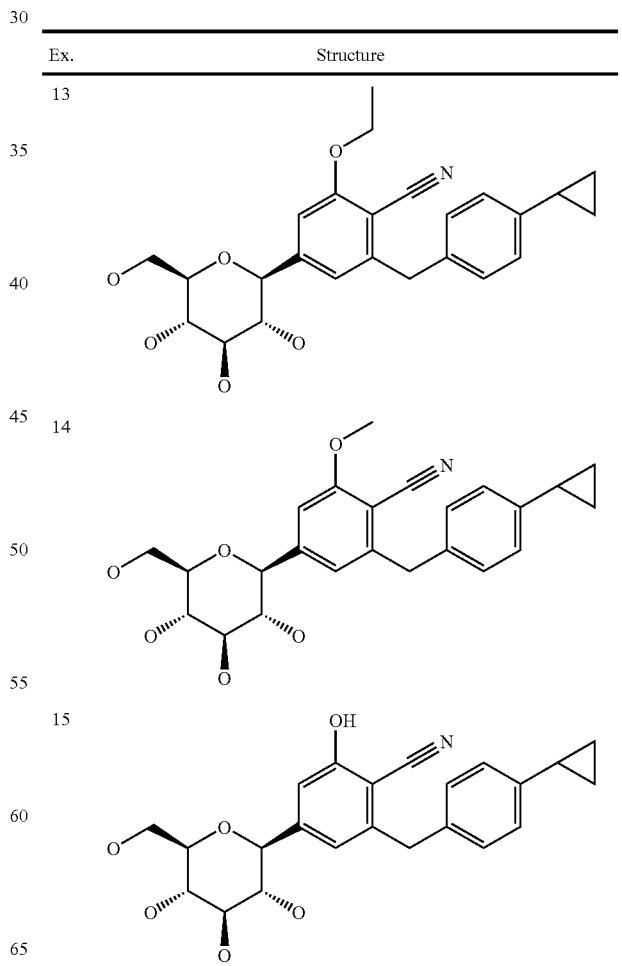

-continued
| Ex. | Structure |
|---|---|
| 16 | 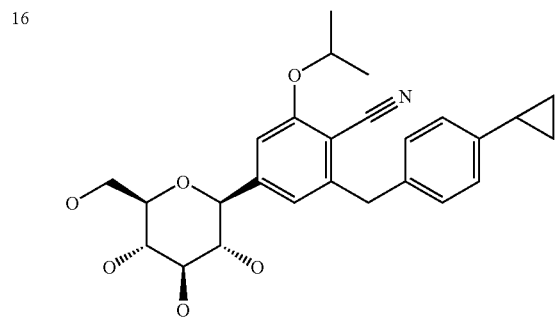 |
| 17 | 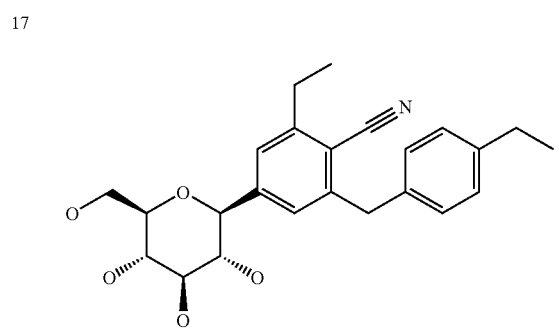 |
| 18 | 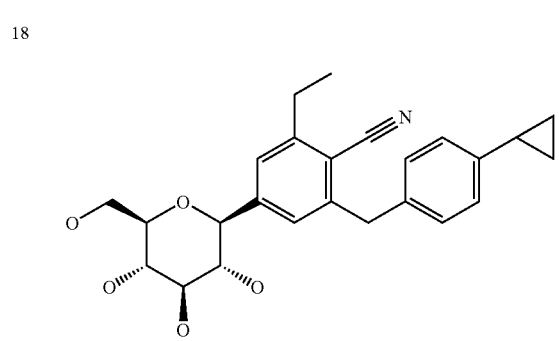 |
| 19 | 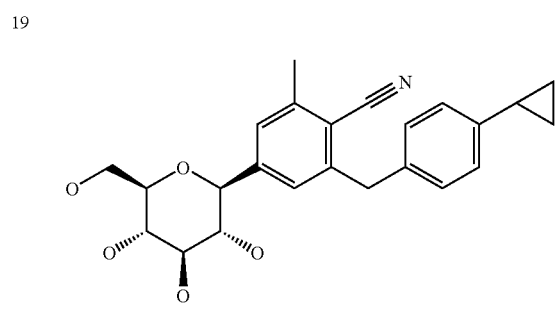 |
| 20 | 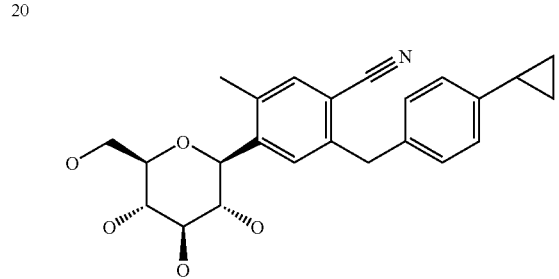 |
-continued
| Ex. | Structure |
|---|---|
| 21 | 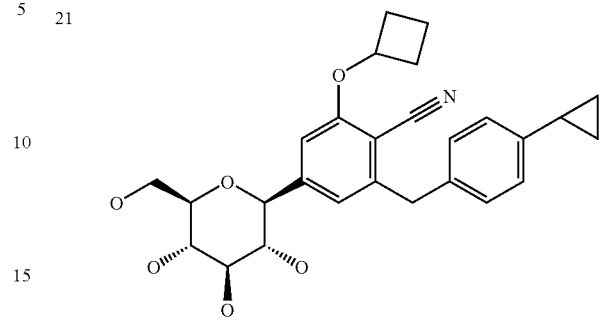 |
| 22 | 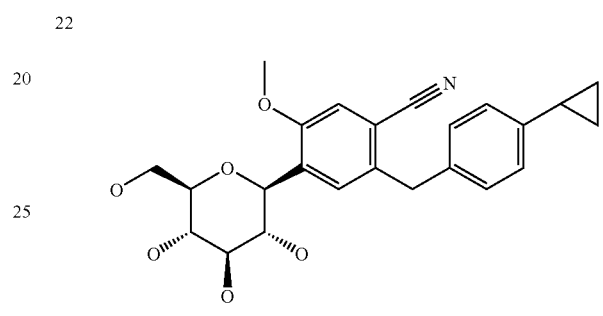 |
| 23 | 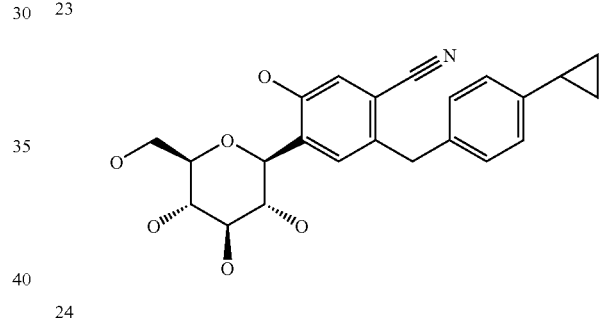 |
| 24 | 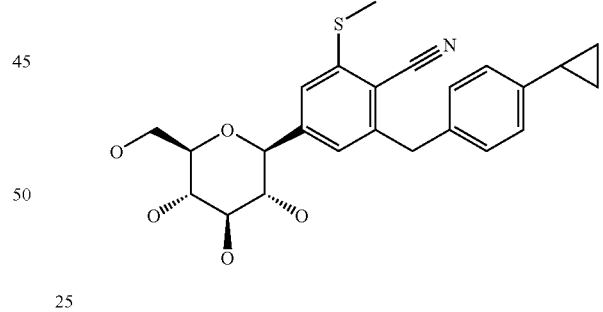 |
| 25 | 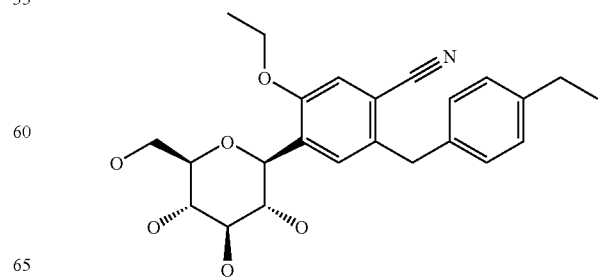 |

-continued
| Ex. | Structure |
|---|---|
| 26 | 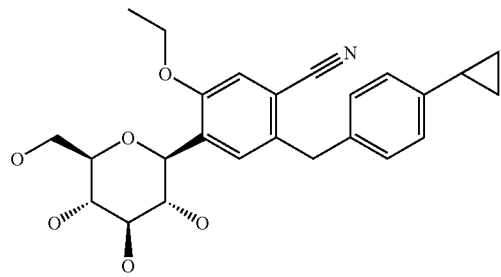 |
| 27 | 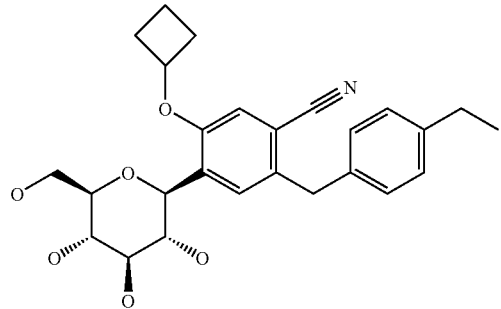 |
| 28 | 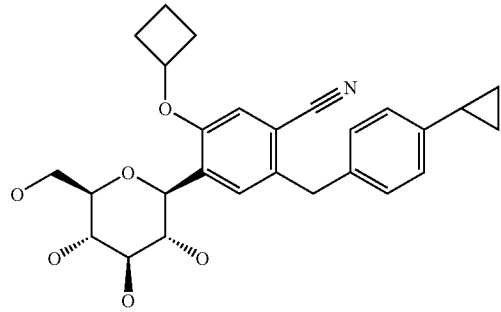 |
| 29 | 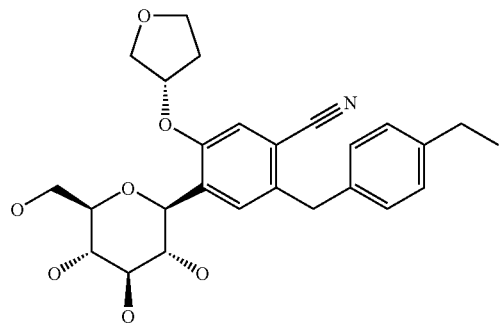 |
| 30 | 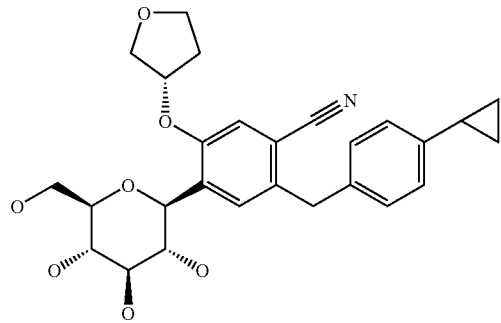 |
-continued
| Ex. | Structure |
|---|---|
| 31 | 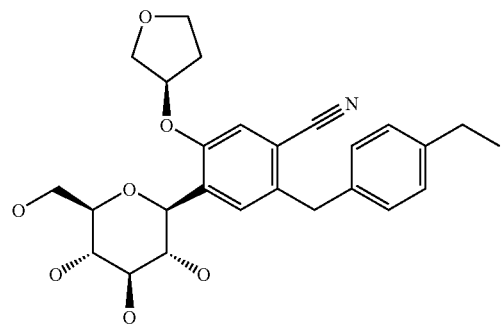 |
| 32 | 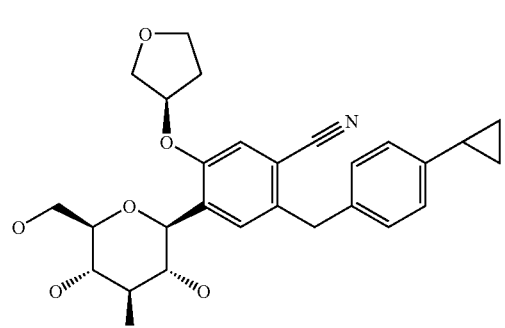 |
| 33 | 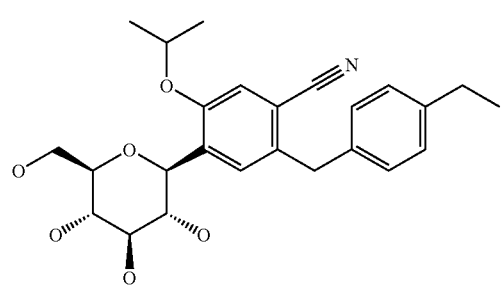 |
| 34 | 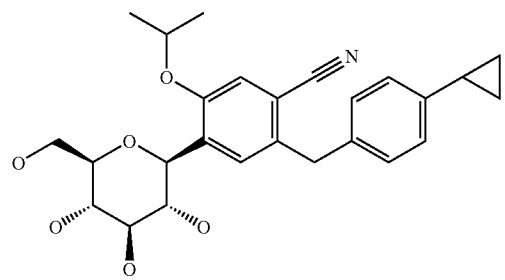 |
| 35 | 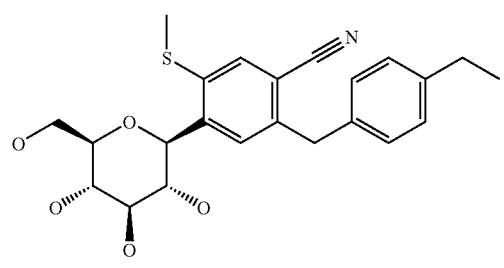 |

| Ex. | Structure |
|---|---|
| 36 | *(chemical structure: pyranose sugar attached to benzene with SMe, CN, and 4-cyclopropylbenzyl substituents)* |

Some examples of formulations will now be described in which the term "active substance" denotes one or more compounds according to the invention, including the salts thereof. In the case of one of the combinations with one or additional active substances as described previously, the term "active substance" also includes the additional active substances.

Example A

Tablets Containing 100 mg of Active Substance

Composition:

1 tablet contains:

| | |
|---|---:|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

Example B

Tablets Containing 150 mg of Active Substance

Composition:

1 tablet contains:

| | |
|---|---:|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

Example C

Hard Gelatine Capsules Containing 150 mg of Active Substance

Composition:

1 capsule contains:

| | |
|---|---:|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

Example D

Suppositories Containing 150 mg of Active Substance

Composition:

1 suppository contains:

| | |
|---|---:|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example E

Ampoules Containing 10 mg Active Substance

Composition:

| | |
|---|---:|
| active substance | 10.0 mg |
| 0.01 N hydrochloric acid q.s. | |
| double-distilled water | ad 2.0 ml |

Preparation:

The active substance is dissolved in the necessary amount of 0.01 N HCl, made isotonic with common salt, filtered sterile and transferred into 2 ml ampoules.

Example F

Ampoules Containing 50 mg of Active Substance

Composition:

| | |
|---|---|
| active substance | 50.0 mg |
| 0.01 N hydrochloric acid q.s. | |
| double-distilled water | ad 10.0 ml |

Preparation:

The active substance is dissolved in the necessary amount of 0.01 N HCl, made isotonic with common salt, filtered sterile and transferred into 10 ml ampoules.

The invention claimed is:

1. Glucopyranosyl-substituted benzyl-benzonitrile derivatives of general formula I

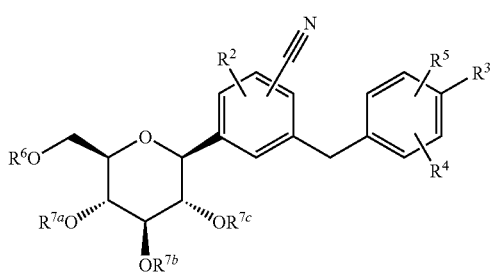

wherein $R^2$ denotes fluorine, chlorine, bromine, iodine, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, hydroxy, $C_{1-4}$-alkoxy, $C_{3-7}$-cycloalkyloxy, $C_{5-7}$-cycloalkenyloxy, $C_{1-4}$-alkylsulfanyl, amino, nitro or cyano, while the above-mentioned alkyl-, alkenyl-, alkynyl-, cycloalkyl- and cycloalkenyl-residues may be mono- or polysubstituted by fluorine and/or mono- or disubstituted by identical or different substituents L2, and while in the above-mentioned $C_{5-6}$-cycloalkyl and $C_{5-6}$-cycloalkenyl rings one or two methylene groups may be replaced independently of one another by O, S, CO, SO or $SO_2$, and $R^3$ hydrogen, fluorine, chlorine, bromine, iodine, $C_{1-6}$-alkyl, $C_{2-6}$-alkynyl, $C_{2-6}$-alkenyl, $C_{3-7}$-cycloalkyl, $C_{3-7}$-cycloalkyl-$C_{1-3}$-alkyl, $C_{5-7}$-cycloalkenyl, $C_{5-7}$-cycloalkenyl-$C_{1-3}$-alkyl, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, hydroxycarbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, arylcarbonylamino, heteroarylcarbonylamino, $C_{1-4}$-alkylsulfonylamino, arylsulfonylamino, $C_{1-6}$-alkoxy, $C_{3-7}$-cycloalkyloxy, $C_{5-7}$-cycloalkenyloxy, aryloxy, heteroaryloxy, $C_{1-4}$-alkylsulfanyl, $C_{1-4}$-alkylsulfinyl, $C_{1-4}$-alkylsulfonyl, $C_{3-7}$-cycloalkylsulfanyl, $C_{3-7}$-cycloalkylsulfinyl, $C_{3-7}$-cycloalkylsulfonyl, $C_{5-7}$-cycloalkenylsulfanyl, $C_{5-7}$-cycloalkenylsulfinyl, $C_{5-7}$-cycloalkenylsulfonyl, arylsulfanyl, arylsulfinyl, arylsulfonyl, heteroarylsulfanyl, heteroarylsulfinyl, heteroarylsulfonyl, amino, hydroxy, cyano and nitro, while the above-mentioned alkyl-, alkenyl-, alkynyl-, cycloalkyl- and cycloalkenyl-residues may be mono- or polysubstituted by fluorine and/or mono- or disubstituted by identical or different substituents L2, and while in the above-mentioned $C_{5-6}$-cycloalkyl and $C_{5-6}$-cycloalkenyl rings one or two methylene groups may be replaced independently of one another by O, S, CO, SO or $SO_2$, and while in the above-mentioned N-heterocycloalkyl rings one methylene group may be replaced by CO or $SO_2$, and $R^4$, $R^5$ independently of one another denote hydrogen, fluorine, chlorine, bromine, iodine, cyano, nitro, $C_{1-3}$-alkyl, $C_{1-3}$-alkoxy, or a methyl- or methoxy-group substituted by 1 to 3 fluorine atoms, L1 independently of one another are selected from among fluorine, chlorine, bromine, iodine, hydroxy, cyano, $C_{1-3}$-alkyl, difluoromethyl, trifluoromethyl, $C_{1-3}$-alkoxy, difluoromethoxy, trifluoromethoxy, amino, $C_{1-3}$-alkyl-amino and di($C_{1-3}$-alkyl)-amino; and L2 independently of one another are selected from among fluorine, chlorine, hydroxy, hydroxyl-$C_{1-4}$-alkyl, $C_{1-4}$-alkoxy, trifluoromethoxy, $C_{1-4}$-alkoxy-$C_{1-4}$-alkyl, cyano, hydroxycarbonyl, ($C_{1-4}$-alkyl)oxycarbonyl, aminocarbonyl, $C_{1-4}$-alkyl, trifluoromethyl, amino, $C_{1-4}$-alkyl-carbonylamino, $C_{1-3}$-alkyl-amino and di($C_{1-3}$-alkyl)-amino; and $R^6$, $R^{7a}$, $R^{7b}$, $R^{7c}$ independently of one another have a meaning selected from among hydrogen, ($C_{1-18}$-alkyl)carbonyl, ($C_{1-18}$-alkyl)oxycarbonyl, arylcarbonyl and aryl-($C_{1-3}$-alkyl)-carbonyl, while the aryl-groups may be mono- or disubstituted independently of one another by identical or different groups L1;

while by the aryl groups mentioned in the definition of the above groups are meant phenyl or naphthyl groups which may be substituted as defined; and while, unless otherwise stated, the above-mentioned alkyl groups may be straight-chain or branched, including tautomers, stereoisomers thereof or mixtures thereof, and physiologically acceptable salts thereof.

2. Glucopyranosyl-substituted benzyl-benzonitrile derivatives according to claim 1 characterized in that $R^2$ denotes fluorine, chlorine, bromine, cyano, $C_{1-4}$-alkyl, $C_{1-4}$-alkyloxy, $C_{3-7}$-cycloalkyl, $C_{3-7}$-cycloalkyloxy or $C_{1-3}$-alkylsulfanyl, while in a $C_{5-6}$-cycloalkyl ring a methylene group may be replaced by O, and wherein any alkyl group or cycloalkyl ring may be mono- or poly-fluorinated and/or mono- or disubstituted with identical or different substituents L2, wherein L2 is defined as in claim 1.

3. Glucopyranosyl-substituted benzyl-benzonitrile derivatives according to claim 1 characterized in that $R^3$ denotes chlorine, bromine, iodine, $C_{1-4}$-alkyl, $C_{3-7}$-cycloalkyl, hydroxyl, $C_{1-4}$-alkyloxy, $C_{3-7}$-cycloalkyloxy, $C_{1-4}$-alkylsulfanyl, $C_{3-7}$-cycloalkylsulfanyl, while in a $C_{5-6}$-cycloalkyl ring a methylene group may be replaced by O, and wherein any alkyl group and cycloalkyl ring may be mono- or poly-fluorinated and/or mono- or disubstituted with identical or different substituents L2, wherein L2 is defined as in claim 1.

4. Glucopyranosyl-substituted benzyl-benzonitrile derivatives according to claim 1 characterized in that $R^6$ denotes hydrogen, ($C_{1-18}$-alkyl)oxycarbonyl, $C_{1-8}$-alkylcarbonyl or benzoyl and $R^{7a}$, $R^{7b}$, $R^{7c}$ represent independently of one another hydrogen, ($C_{1-18}$-alkyl)oxycarbonyl, ($C_{1-8}$-alkyl)carbonyl or benzoyl.

5. Glucopyranosyl-substituted benzyl-benzonitrile derivatives according to claim 4 characterized in that $R^6$, $R^{7a}$, $R^{7b}$, $R^{7c}$ represent hydrogen.

6. Physiologically acceptable salts of the compounds according to claim 1 with inorganic or organic acids.

7. Pharmaceutical composition, comprising a compound according to claim 1 or a physiologically acceptable salt, optionally together with one or more inert carriers and/or diluents.

8. A method for the treatment of diseases or conditions which can be influenced by inhibiting the sodium-dependent glucose cotransporter SGLT comprising administering to a patient in need thereof a therapeutically effective amount of a compound according to claim 1 or a physiologically acceptable salt thereof with an inorganic or organic acid wherein the disease or condition is selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

9. A Method for the treatment of one or more metabolic disorders comprising administering to a patient in need thereof a therapeutically effective amount of a compound according to claim 1 or a physiologically acceptable salt thereof with an inorganic or organic acid wherein the metabolic disorder is selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

10. A method for inhibiting the sodium-dependent glucose cotransporter SGLT2 comprising administering to a patient a compound according to claim 1 or a physiologically acceptable salt thereof with an inorganic or organic acid.

11. A method for treating the degeneration of pancreatic beta cells and/or for improving and/or restoring the functionality of pancreatic beta cells_comprising administering to a patient in need thereof a therapeutically effective amount of a compound according to claim 1 or a physiologically acceptable salt thereof with an inorganic or organic acid.

12. A method for treating diseases or conditions attributed to an abnormal accumulation of liver fat comprising administering to a patient in need thereof a therapeutically effective amount of a compound according to claim 1 or a physiologically acceptable salt thereof with an inorganic or organic acid.

13. A method for preparing a diuretic and/or antihypertensive comprising a compound according to claim 1 or a physiologically acceptable salt thereof with an inorganic or organic acid.

14. A process for preparing a compound according to claim 1 characterised in that a) a compound of general formula II

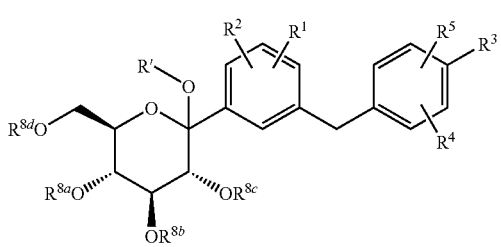

wherein $R^1$ denotes cyano, chlorine or bromine;

R' denotes H, $C_{1-4}$-alkyl, ($C_{1-18}$-alkyl)carbonyl, ($C_{1-18}$-alkyl)oxycarbonyl, arylcarbonyl and aryl-($C_{1-3}$-alkyl)-carbonyl, wherein the alkyl or aryl groups may be mono- or polysubstituted by halogen;

$R^{8a}$, $R^{8b}$, $R^{8c}$, $R^{8d}$ independently of one another have one of the meanings given hereinbefore and hereinafter for the groups $R^6$, $R^{7a}$, $R^{7b}$, $R^{7c}$, or denote a benzyl or allyl group or a $R^aR^bR^cSi$ group or a ketal or acetal group, particularly an alkylidene or arylalkylidene ketal or acetal group, while in each case two adjacent groups $R^{8a}$, $R^{8b}$, $R^{8c}$, $R^{8d}$ may form a cyclic silyl ketal, ketal or acetal group or a 1,2-di($C_{1-3}$-alkoxy)-1,2-di($C_{1-3}$-alkyl)-ethylene bridge, while the above-mentioned ethylene bridge forms, together with two oxygen atoms and the two associated carbon atoms of the pyranose ring, a substituted dioxane ring, particularly a 2,3-dimethyl-2,3-di($C_{1-3}$-alkoxy)-1,4-dioxane ring, and while alkyl, aryl and/or benzyl groups may be mono- or polysubstituted by halogen or $C_{1-3}$-alkoxy, and while benzyl groups may also be substituted by a di-($C_{1-3}$-alkyl) amino group; and $R^a$, $R^b$, $R^c$ independently of one another denote $C_{1-4}$-alkyl, aryl or aryl-$C_{1-3}$-alkyl, wherein the aryl or alkyl groups may be mono- or polysubstituted by halogen;

while by the aryl groups mentioned in the definition of the above groups are meant phenyl or naphthyl groups, preferably phenyl groups;

and wherein the groups $R^2$ to $R^6$, $R^{7a}$, $R^{7b}$, $R^{7c}$ are defined as in claim 1;

is reacted with a reducing agent in the presence of a Lewis or Brønsted acid, while any protective groups present are cleaved simultaneously or subsequently; if in the compound of the formula II $R^1$ denotes Cl or Br, then in a subsequent transformation the respective halogen atom of $R^1$ is replaced by a cyano group; or b) a compound of general formula III

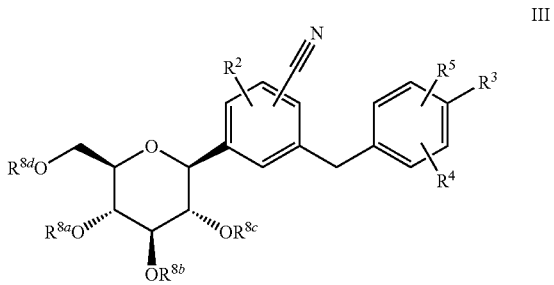

wherein $R^{8a}$, $R^{8b}$, $R^{8c}$, $R^{8d}$ and $R^2$ to $R^5$ are defined as in claim 1, but at least one of the groups $R^{8a}$, $R^{8b}$, $R^{8c}$, $R^{8d}$ does not denote hydrogen, is hydrolysed to yield a compound of the formula I defined as in claim 1 wherein $R^6$, $R^{7a}$, $R^{7b}$ and $R^{7c}$ denote hydrogen, and if desired a compound of formula I thus obtained wherein $R^6$ denotes a hydrogen atom, is converted by acylation into a corresponding acyl compound of general formula I, and/or if necessary any protective group used in the reactions described above is cleaved and/or if desired a compound of formula I thus obtained is resolved into its stereoisomers and/or if desired a compound of formula I thus obtained is converted into the salts thereof.

15. A process for preparing compounds of general formula II

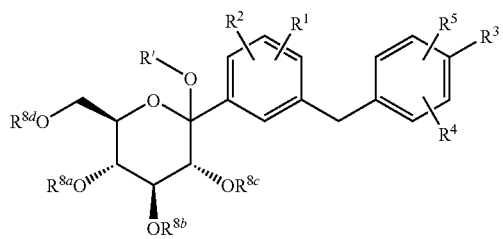

wherein
- $R^1$ denotes cyano, chlorine or bromine;
- R' denotes H, $C_{1-4}$-alkyl, $(C_{1-18}$-alkyl)carbonyl, $(C_{1-18}$-alkyl)oxycarbonyl, arylcarbonyl and aryl-$(C_{1-3}$-alkyl)-carbonyl, wherein the alkyl or aryl groups may be mono- or polysubstituted by halogen;
- $R^{8a}$, $R^{8b}$, $R^{8c}$, $R^{8d}$ independently of one another has one of the meanings given for the groups $R^6$, $R^{7a}$, $R^{7b}$, $R^{7c}$, or denote a benzyl or allyl group or a $R^a R^b R^c$Si group or a ketal or acetal group, while in each case two adjacent groups $R^{8a}$, $R^{8b}$, $R^{8c}$, $R^{8d}$ may form a cyclic silyl ketal, ketal or acetal group or may form, with two oxygen atoms of the pyranose ring, a substituted 2,3-oxydioxane ring, particularly a 2,3-dimethyl-2,3-di($C_{1-3}$-alkoxy)-1,4-dioxane ring, and while alkyl, aryl and/or benzyl groups may be mono- or polysubstituted by halogen or $C_{1-3}$-alkoxy, and while benzyl groups may also be substituted by a di-($C_{1-3}$-alkyl)amino group; and
- $R^a$, $R^b$, $R^c$ independently of one another denote $C_{1-4}$-alkyl, aryl or aryl-$C_{1-3}$-alkyl, while the alkyl or aryl groups may be mono- or polysubstituted by halogen;

while by the aryl groups mentioned in the definition of the above groups are meant phenyl or naphthyl groups, preferably phenyl groups;

and $R^2$ to $R^6$, $R^{7a}$, $R^{7b}$, $R^{7c}$ are defined as in claim 1, wherein an organometallic compound (V) which may be obtained by halogen-metal exchange or by inserting a metal in the carbon-halogen bond of a halogen-benzylbenzene compound of general formula IV

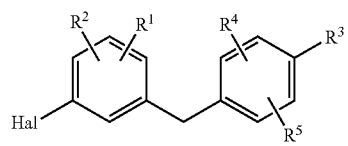

wherein Hal denotes Cl, Br and I and $R^1$ denotes CN, Cl or Br and $R^2$ to $R^5$ are defined as in claim 1, and optionally subsequent transmetallation, is added to a gluconolactone of general formula VI

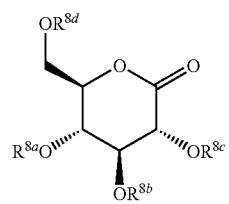

wherein $R^{8a}$, $R^{8b}$, $R^{8c}$, $R^{8d}$ are defined as in claim 1, and then the resulting adduct is reacted with water or an alcohol R'—OH, while R' denotes optionally substituted $C_{1-4}$-alkyl, in the presence of an acid and optionally the product obtained in the reaction with water wherein R' denotes H is converted, in a subsequent reaction, with an acylating agent into the product of formula II wherein R' denotes $(C_{1-18}$-alkyl)carbonyl, $(C_{1-18}$-alkyl)oxycarbonyl, arylcarbonyl or aryl-$(C_{1-3}$-alkyl)-carbonyl, which may be substituted as specified.

16. A compound of general formula II

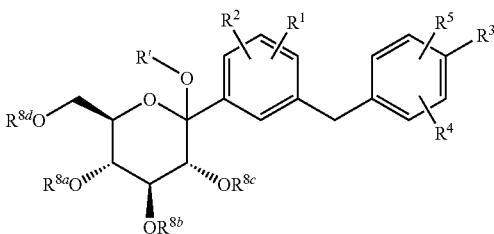

wherein R', $R^{8a}$, $R^{8b}$, $R^{8c}$, $R^{8d}$ and $R^1$ to $R^5$ are defined as in claim 15.

* * * * *